United States Patent
Jafri et al.

(10) Patent No.: US 11,066,461 B2
(45) Date of Patent: Jul. 20, 2021

(54) METHOD FOR PREVENTING OR TREATING NOSOCOMIAL PNEUMONIA

(71) Applicant: MedImmune Limited, Cambridge (GB)

(72) Inventors: Hasan Jafri, Gaithersburg, MD (US); Antonio Digiandomenico, Gaithersburg, MD (US); Michael McCarthy, Gaithersburg, MD (US); Xiang-Qing Yu, Gaithersburg, MD (US); Charles K. Stover, Gaithersburg, MD (US); Brian Bishop, Gaithersburg, MD (US)

(73) Assignee: MEDIMMUNE LIMITED, Cambridge (GB)

( * ) Notice: Subject to any disclaimer, the term of this patent is extended or adjusted under 35 U.S.C. 154(b) by 0 days.

(21) Appl. No.: 15/779,189

(22) PCT Filed: Nov. 28, 2016

(86) PCT No.: PCT/US2016/063865
§ 371 (c)(1),
(2) Date: May 25, 2018

(87) PCT Pub. No.: WO2017/095744
PCT Pub. Date: Jun. 8, 2017

(65) Prior Publication Data
US 2018/0355026 A1    Dec. 13, 2018

Related U.S. Application Data

(60) Provisional application No. 62/260,935, filed on Nov. 30, 2015.

(51) Int. Cl.
C07K 16/12    (2006.01)
A61P 31/04    (2006.01)
(Continued)

(52) U.S. Cl.
CPC ......... *C07K 16/1214* (2013.01); *A61K 39/40* (2013.01); *A61K 45/06* (2013.01);
(Continued)

(58) Field of Classification Search
CPC .. A61K 2039/505; A61K 39/40; A61K 45/06; C07K 16/1214; C07K 2317/21;
(Continued)

(56) References Cited

U.S. PATENT DOCUMENTS 5,585,089 A    12/1996 Queen et al.
5,693,761 A    12/1997 Queen et al.
(Continued)

FOREIGN PATENT DOCUMENTS

WO    WO-2012170807 A2    12/2012
WO    WO-2013/070615 A1    5/2013
(Continued)

OTHER PUBLICATIONS

Que et al.,., "Assessment of panobacumab as adjunctive immunotherapy for the treatment of nosocomial Pseudomonas aeruginosa pneumonia" Eur J Clin Microbiol Infect Dis; epub May 20, 2014; vol. 33; No. 10; pp. 1861-1867. (Year: 2014).*
(Continued)

*Primary Examiner* — Jana A Hines
(74) *Attorney, Agent, or Firm* — Sterne, Kessler, Goldstein & Fox P.L.L.C.

(57) ABSTRACT

A method for preventing or treating nosocomial diseases, e.g., diseases caused by *Pseudomonas aeruginosa*, is provided. The method includes administering to a susceptible human subject a specified dose of a bispecific antibody that specifically binds *Pseudomonas aeruginosa* Psl and PcrV.

8 Claims, 3 Drawing Sheets

Figure 1:
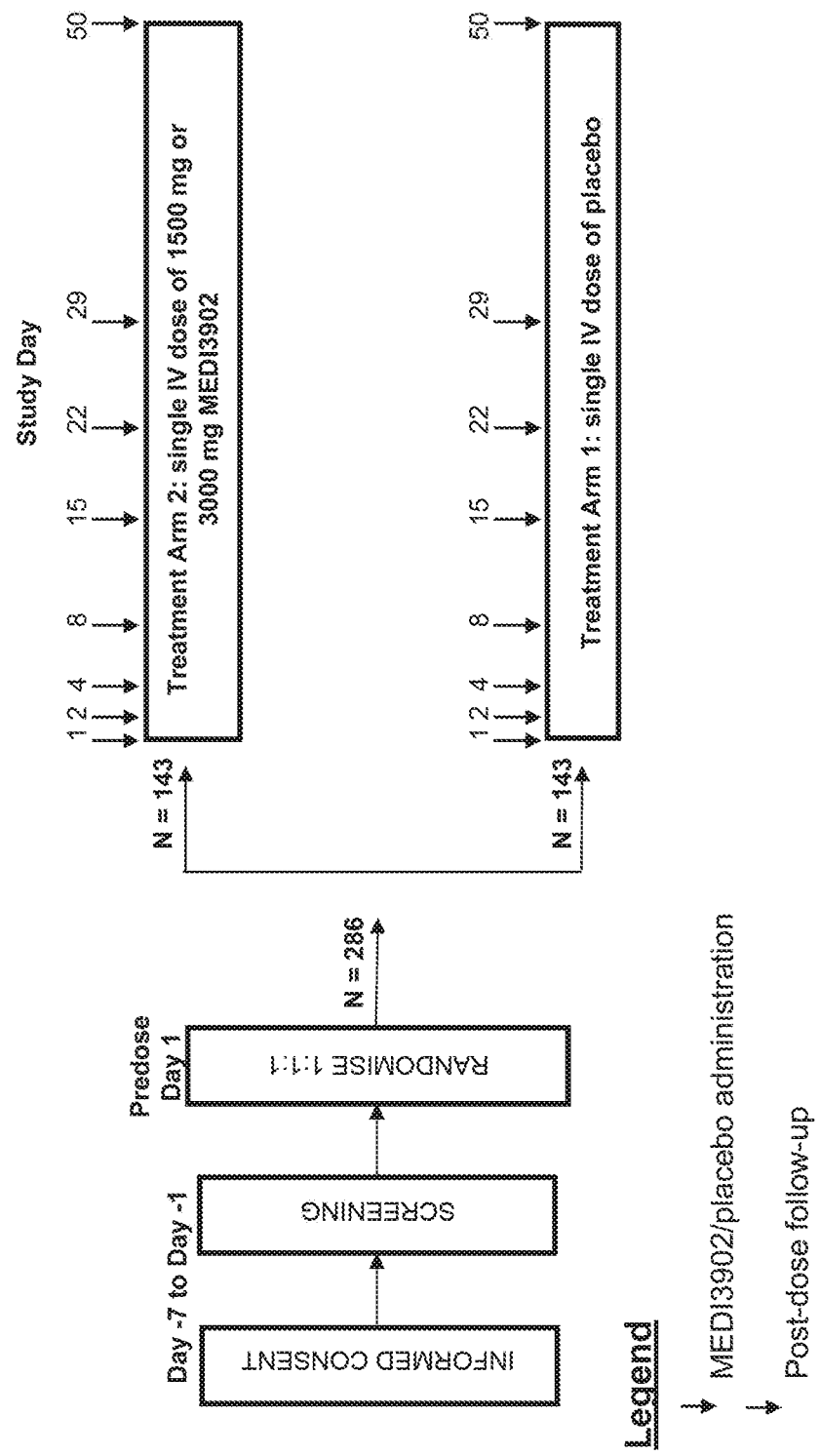

Specification includes a Sequence Listing.

(51) Int. Cl.
*A61K 39/40* (2006.01)
*A61K 45/06* (2006.01)
*C07K 16/46* (2006.01)
*A61K 39/00* (2006.01)

(52) U.S. Cl.
CPC .......... *A61P 31/04* (2018.01); *C07K 16/468* (2013.01); *A61K 2039/505* (2013.01); *C07K 2317/21* (2013.01); *C07K 2317/31* (2013.01); *C07K 2317/76* (2013.01)

(58) Field of Classification Search
CPC .............. C07K 2317/31; C07K 16/468; C07K 2317/76; A61P 31/04
See application file for complete search history.

(56) References Cited

U.S. PATENT DOCUMENTS

| | | | |
|---|---|---|---|
| 5,693,762 | A | 12/1997 | Queen et al. |
| 5,892,019 | A | 4/1999 | Schlom et al. |
| 5,939,598 | A | 8/1999 | Kucherlapati et al. |
| 6,180,370 | B1 | 1/2001 | Queen et al. |
| 9,403,901 | B2 | 8/2016 | Digiandomenico |
| 10,370,436 | B2 | 8/2019 | Digiandomenico |
| 10,597,439 | B2 | 3/2020 | Digiandomenico |
| 10,844,114 | B2 | 11/2020 | Digiandomenico |
| 2016/0115250 | A1 | 4/2016 | Digiandomenico |
| 2019/0309095 | A1 | 10/2019 | Digiandomenico |
| 2019/0322726 | A1 | 10/2019 | Digiandomenico |
| 2020/0317757 | A1 | 10/2020 | Digiandomenico |

FOREIGN PATENT DOCUMENTS

| | | | | |
|---|---|---|---|---|
| WO | WO-2014/074528 A2 | | 5/2014 | |
| WO | WO-2014074528 A2 | * | 5/2014 | ............ A61K 45/06 |
| WO | WO-2014186358 A2 | | 11/2014 | |
| WO | 20150171504 A1 | | 11/2015 | |
| WO | WO 2015/171504 | * | 11/2015 | ......... C07K 16/1214 |
| WO | WO-2015171504 A1 | * | 11/2015 | ............ C07K 16/22 |
| WO | WO-2015/196011 A1 | | 12/2015 | |
| WO | WO-2017095744 A1 | | 6/2017 | |

OTHER PUBLICATIONS

Que et al., Eur J Clin Microbiol Infect Dis ePub May 20, 2014. vol. 33; No(10). pp. 1861-1867. (Year: 2014).*

Khan et al., Asian Pacific J. of Tropical Biomedicine. vol. 7, Issue 5, May 2017, pp. 478-482). (Year: 2017).*

Que et al. "Assessment of panobacumab as adjunctive immunotherapy for the treatment of nosocomial Pseudomonas aeruginosa pneumonia", Eur j Clin Microbiol Infect Dis; ePub May 20, 2014; vol. 33; No. 10; pp. 1861-1867.

Australian Patent Application No. 2016362202, Examination Report No. 1, dated Feb. 20, 2019.

European Patent Application No. 16871318.8, Extended European Search Report, dated Jul. 1, 2019.

International Application No. PCT/US16/63865, International Search Report and Written Opinion, dated Feb. 14, 2017.

Chothia et al., Canonical structures for the hypervariable regions of immunoglobulins, J. Mol. Biol., 196(4):901-17 (1987).

DiGiandomenico et al., Identification of broadly protective human antibodies to Pseudomonas aeruginosa exopolysaccharide Psl by phenotypic screening, J. Exp. Med., 209(7):1273-87 (2012).

Esperatti et al., Nosocomial pneumonia in the intensive care unit acquired by mechanically ventilated versus nonventilated patients, Am. J. Respir. Crit Care Med., 182(12):1533-9 (2010).

Jones, Microbial etiologies of hospital-acquired bacterial pneumonia and ventilator-associated bacterial pneumonia, Clin. Infect. Dis., 51 Suppl 1:S81-7 (2010).

Kabat et al., Sequences of Proteins of Immunological Interest, U.S. Department of Health and Human Services (1983).

Kyaw et al., The influence of chronic illnesses on the incidence of invasive pneumococcal disease in adults, J. Infect. Dis., 192(3):377-86 (2005).

Mabry et al., Therapeutic bispecific antibodies: The selection of stable single-chain fragments to overcome engineering obstacles, IDrugs, 13(8):543-9 (2010).

Strohlein et al., The trifunctional antibody catumaxomab in treatment of malignant ascites and peritoneal carcinomatosis, Future Oncol., 6(9):1387-94 (2010).

Zahar et al., Predicting the risk of documented ventilator-associated pneumonia for benchmarking: construction and validation of a score, Crit. Care Med., 37(9):2545-51 (2009).

International Preliminary Report on Patentability dated Feb. 14, 2017, in International Application No. PCT/US2016/063865, ISA, United States, 6 pages.

Co-Pending U.S. Appl. No. 16/789,790, filed Feb. 13, 2020, Digiandomenico; A, et al. (Un-Published).

Hernandez, A.C., et al., "Interim Pharmacokinetic Analysis from the Evade Phase 2 Clinical Trial of MEDI3902, A bispecific Monoclonal Antibody Against PCRV and PSL of Pseudomonas Aeruginosa," Retrieved on Jan. 29, 2021, retrieved from: https://www.imi.europa.eu/sites/default/files/events/2018/ScientificSymposium/25-%20Ana%20Catalina.pdf, 1 page, (Oct. 2018).

U.S. Department of Health and Human Services, "Guidance for Industry: Estimating the Maximum Safe Starting Dose in Initial Clinical Trials for Therapeutics in Adult Healthy Volunteers," Pharmacology and Toxicology: 30 pages, Food and Drug Administration, United States (2005).

Co-Pending U.S. Appl. No. 17/073,879, filed Oct. 19, 2020, inventor Digiandomenico, A, et al. (Un-Published).

* cited by examiner

METHOD FOR PREVENTING OR TREATING NOSOCOMIAL PNEUMONIA

CROSS-REFERENCE TO RELATED APPLICATIONS

This application is a U.S. National Stage application of International Application No. PCT/US2016/063865, filed on Nov. 28, 2016, said International Application No. PCT/US2016/063865 claims benefit under 35 U.S.C. § 119(e) of the U.S. Provisional Application No. 62/260,935, Nov. 30, 2015. Each of the above listed applications are incorporated by reference herein in its entirety for all purposes.

REFERENCE TO THE SEQUENCE LISTING

This application incorporates by reference a Sequence Listing submitted with International Application No. PCT/US2016/063865.

SEQUENCE LISTING

The instant application contains a Sequence Listing which has been submitted electronically in ASCII format and is hereby incorporated by reference in its entirety. Said ASCII copy, created on Nov. 17, 2016, is named PSEUD-200-WO-PCT_SL.txt and is 22,415 bytes in size.

BACKGROUND

*Pseudomonas aeruginosa* (*P. aeruginosa*) is an important nosocomial pathogen, and pneumonia is one of its most concerning manifestations. Mechanical ventilation is the most important risk factor for nosocomial pneumonia caused by *P. aeruginosa*, with cumulative risk increasing with the duration of ventilation (Zahar, J R, et al. *Crit Care Med.* 2009 September; 37(9):2545-51). In one study, *P. aeruginosa* accounted for 13% of cases of microbiologically confirmed pneumonia acquired in the intensive care unit (ICU) by patients who were not mechanically ventilated, and 24% of cases in those who were (Esperatti et al, *Am J Respir Care Med.* 2010 Dec. 15:182(12):1533-9). In a review of global epidemiology data, *P. aeruginosa* caused approximately 27% of ventilator-associated pneumonia (VAP, Jones, *Clin Infect Dis.* 2010 Aug. 1;51 Suppl 1:S81-7). Respiratory tract colonisation with *P. aeruginosa* is another important risk factor (Rehm and Kollef, Poster #367, 43rd Critical Care Congress Society of Critical Care Medicine (SCCM); 9-13 Jan. 2014, San Francisco Calif. USA). Despite the existence of antibiotics, pneumonia, particularly VAP, due to *P. aeruginosa* remains associated with significant mortality ad morbidity, increased ICU and hospital length of stay, and substantial economic burden.

Patients in the ICU are at risk for developing serious pneumonia infection and mechanical ventilation increases the risk for pneumonia in the ICU. *P. aeruginosa* is a leading cause of ICU pneumonia that contributes significantly to increased hospital stays (55.4 days v. 7.2 days), ICU stays (14.8 days v. 1.1 days), and greater need for mechanical ventilation (62.3% v. 7.4%), as well as patient mortality (20.2% v. 3.1% of). (Kyaw M H, et al. *J Infect Dis.* (2005) 192(3):377-386). Additionally, multi-drug resistance has complicated the management of *P. aeruginosa* infection. With limited antimicrobial therapeutic options, consideration of new approaches, such as immunoprophylaxis for the prevention of *P. aeruginosa* would address an important unmet need.

MEDI3902 is a bivalent, bispecific human immunoglobulin G1 (IgG1) kappa monoclonal antibody (mAb) that selectively binds to both the PcrV protein and Psl exopolysaccharide on the surface of *P. aeruginosa*. Pharmacology studies have demonstrated that MEDI3902 is capable of mediating three distinct mechanisms of action: anticytotoxicity, opsonophagocytosis and killing, and inhibition of *P. aeruginosa* attachment to cells. Binding to PcrV on intact *P. aeruginosa* prevents type 3 secretion (T3S) injectisome-mediated cytotoxicity and damage to host cells. Binding to Psl mediates opsonophagocytic killing (OPK) of *P. aeruginosa* by host effector cells and inhibits *P. aeruginosa* attachment to host epithelial cells (DiGiandomenico et al, *J Exp Med.* 2012 Jul. 2:209(7):1273-87).

MEDI3902 was highly protective in *P. aeruginosa* murine infection models. See, e.g., in PCT Publication No. WO 2013/070615, PCT Publication No. WO 2014/074528, PCT Application No. PCT/US2015/029063, and PCT Application No. PCT/US2015/036576. Moreover, MEDI3902 provided synergistic enhancement of antibiotic therapy against *P. aeruginosa* pneumonia with distinct antibiotic classes against both antibiotic-sensitive and antibiotic-resistant *P. aeruginosa*.

SUMMARY

This disclosure provides a method of preventing or treating nosocomial infection in a susceptible human subject, where the method includes administering to the subject about 500 to about 3000 mg, e.g., about 500, 600, 700, 750, 1000, 1500 or about 3000 mg, of a bispecific antibody that specifically binds *Pseudomonas aeruginosa* Psl and PcrV (e.g., MEDI3902), and monitoring the subject for symptoms through 21 days from the day of administration. According to the method, at 21 days post-administration the subject can be symptom-free or can display less severe symptoms relative to a cohort of susceptible human subjects administered a placebo. In certain aspects the nosocomial infection can be pneumonia, e.g., *Pseudomonas aeruginosa* pneumonia, bacteremia, bone infection, joint infection, skin infection, burn infection, wound infection, or any combination thereof.

This disclosure further provides a method of preventing or treating pneumonia, e.g., *Pseudomonas aeruginosa* pneumonia, in a susceptible human subject, where the method includes administering to the subject about 500 to about 3000 mg, e.g., about 500, 600, 700, 750, 1000, 1500 or about 3000 mg, of a bispecific antibody that specifically binds *Pseudomonas aeruginosa* Psl and PcrV (e.g., MEDI3902), and monitoring the subject for pneumonia symptoms through 21 days from the day of administration. According to the method, at least at 21 days post-administration the subject can be pneumonia-free or can display less severe symptoms relative to a cohort of susceptible human subjects administered a placebo.

In some embodiments, the serum target level of the bispecific antibody (e.g., MEDI3902) is at least about 1 µg/mL, at least about 2 µg/mL, at least about 3 µg/mL, at least about 4 µg/mL, or at least about 5 µg/mL. In other embodiments, the serum target level of the bispecific antibody (e.g., MEDI3902) is at least about 1.7 µg/mL. In further embodiments, the serum target level of the bispecific antibody (e.g., MEDI3902) is at least about 5.3 µg/mL. In some embodiments, the administration produces a serum level of the bispecific antibody (e.g., MEDI3902) of at least 1 µg/mL, at least about 2 µg/mL, at least about 3 µg/mL, at least about 4 µg/mL, or at least about 5 µg/mL through day 21 following administration of the bispecific antibody. In other embodiments, the administration produces a serum level of the bispecific antibody (e.g., MEDI3902) of at least 1.7 µg/mL through day 21 following administration of the bispecific antibody. In further embodiments, the serum target level of the bispecific antibody (e.g., MEDI3902) is at least about 5.3 µg/mL.

In some embodiments, the method of preventing or treating nosocomial infection in a susceptible human subject comprises administering a bispecific antibody comprising a binding domain which specifically binds to P. aeruginosa Psl comprising a set of complementarity determining regions (CDRs): HCDR1-Psl, HCDR2-Psl, HCDR3-Psl, LCDR1-Psl, LCDR2-Psl, and LCDR3-Psl, wherein HCDR1-Psl has the amino acid sequence of SEQ ID NO: 10. HCDR2-Psl has the amino acid sequence of SEQ ID NO: 11, HCDR3-Psl has the amino acid sequence of SEQ ID NO: 12, LCDR1-Psl has the amino acid sequence of SEQ ID NO: 13, LCDR2-Psl has the amino acid sequence of SEQ ID NO: 14, and LCDR3-Psl has the amino acid sequence of SEQ ID NO: 15; and a binding domain which specifically binds to P. aeruginosa PcrV comprising a set of CDRs: HCDR1-PcrV, HCDR2-PcrV, HCDR3-PcrV, LCDR1-PcrV, LCDR2-PcrV, and LCDR3-PcrV, wherein HCDR1-PcrV has the amino acid sequence of SEQ ID NO: 2, HCDR2-PcrV has the amino acid sequence of SEQ ID NO: 3 HCDR3-PcrV has the amino acid sequence of SEQ ID NO: 4, LCDR1-PcrV has the amino acid sequence of SEQ ID NO: 6, LCDR2-PcrV has the amino acid sequence of SEQ ID NO: 7, and LCDR3-PcrV has the amino acid sequence of SEQ ID NO. 8. In certain aspects, the bispecific antibody has a heavy chain and a light chain. The heavy chain includes the formula VH-CH1-H1-L1-S-L2-H2-CH2-CH3, where VH is an anti-P. aeruginosa PcrV heavy chain variable domain including the amino acid sequence of SEQ ID NO: 1, CH1 is a heavy chain constant region domain-1, H1 is a first heavy chain hinge region fragment, L1 is a first linker, S is an anti-P. aeruginosa Psl ScFv molecule including the amino acid sequence of SEQ ID NO: 9, L2 is a second linker, H2 is a second heavy chain hinge region fragment, CH2 is a heavy chain constant region domain-2, and CH3 is a heavy chain constant region domain-3. The light chain includes the formula VL-CL, where VL is an anti-P. aeruginosa PcrV light chain variable domain including the amino acid sequence of SEQ ID NO. 5 and CL includes an antibody light chain kappa constant region or an antibody light chain lambda region. In certain aspects, CH1 can include the amino acid sequence of SEQ ID NO: 16. In certain aspects L1 and L2 can be the same or different, and can independently include (a) [GGGGS]n, where n is 0, 1, 2, 3, 4, or 5 (SEQ ID NO: 23), (b) [GGGG]n, where n is 0, 1, 2, 3, 4, or 5 (SEQ ID NO: 24), or a combination of (a) and (b). In certain aspects, H1 can include the amino acid sequence EPKSC (SEQ ID NO: 17). In certain aspects, H2 can include the amino acid sequence DKTHTCPPCP (SEQ ID NO: 18). In certain aspects, CH2-CH3 can include the amino acid sequence of SEQ ID NO: 19. In certain aspects CH2-CH3 can include the amino acid sequence of SEQ ID NO: 20. In certain aspects, the heavy chain of the bispecific antibody can include the amino acid sequence of SEQ ID NO: 21, and the light includes the amino acid sequence of SEQ ID NO: 22.

According to the methods provided herein, the bispecific antibody (e.g. MEDI3902) can be administered as a single intravenous (IV) infusion.

According to the methods provided herein, at the time of the administration of the bispecific antibody the subject can be colonized with Pseudomonas aeruginosa in the respiratory tract, e.g., the lower respiratory tract. In certain aspects, the subject does not have pneumonia symptoms at the time of administration. In certain aspects, the subject's respiratory tract is colonized with P. aeruginosa one, two, three, or four days prior to administration of the bispecific antibody. Colonization can be measured, e.g., by detection of P. aeruginosa in a tracheal aspirate within 36 hours prior to administration of the bispecific antibody. In certain aspects, the subject's respiratory tract can be additionally colonized by Staphylococcus aureus at the time of administration of the bispecific antibody.

In certain aspects, the subject is about to be hospitalized, is currently hospitalized, e.g., in an intensive care unit (ICU), was, recently hospitalized, is on a mechanical ventilator, e.g., is intubated or ventilated through an endotracheal or nasotracheal tube, or any combination thereof. According to the methods provided herein, the administration of the bispecific antibody can reduce the risk of pneumonia while on mechanical ventilation, or after mechanical ventilation is no longer required.

In certain aspects a microbiologic confirmation of pneumonia can include a respiratory specimen positive for P. aeruginosa by culture, a blood culture positive for P. aeruginosa, a pleural fluid aspirate or lung tissue culture positive for P. aeruginosa, or any combination thereof.

In certain aspects, the subject has not received antibiotics considered active against the P. aeruginosa strain with which the subject is colonized prior to administration of the bispecific antibody (e.g., MEDI3902). In other aspects, the method can further include administering an antibiotic to the subject. In certain aspects, the P. aeruginosa strain with which the subject is colonized can sensitive to the antibiotic, or can be resistant or partially resistant to the antibiotic. Where an antibiotic as administered it can be administered prior to administration of the bispecific antibody, concurrently with administration of the bispecific antibody, following administration of the bispecific antibody, or any combination thereof.

In certain aspects the method cars further include administering an antihistamine to the subject. Where an antihistamine is administered it can be administered prior to administration of the bispecific antibody, concurrently with administration of the bispecific antibody, following administration of the bispecific antibody, or any combination thereof.

BRIEF DESCRIPTION OF THE DRAWINGS/FIGURES

FIG. 1 provides a flow diagram of the Phase IIb clinical trial study protocol. ADA=anti-drug antibody; IV=intravenous; N=number of subjects; PK=pharmacokinetics. Efficacy will be assessed through 21 days postdose (Day 22); safety, PK and ADA will be assessed through 49 days postdose (Day 50). The sample size can be modified after approximately 50% of the subjects are enrolled and followed through 21 days postdose based on blinded assessment of the event rate and/or attrition rate in the overall population.

Figure 2:
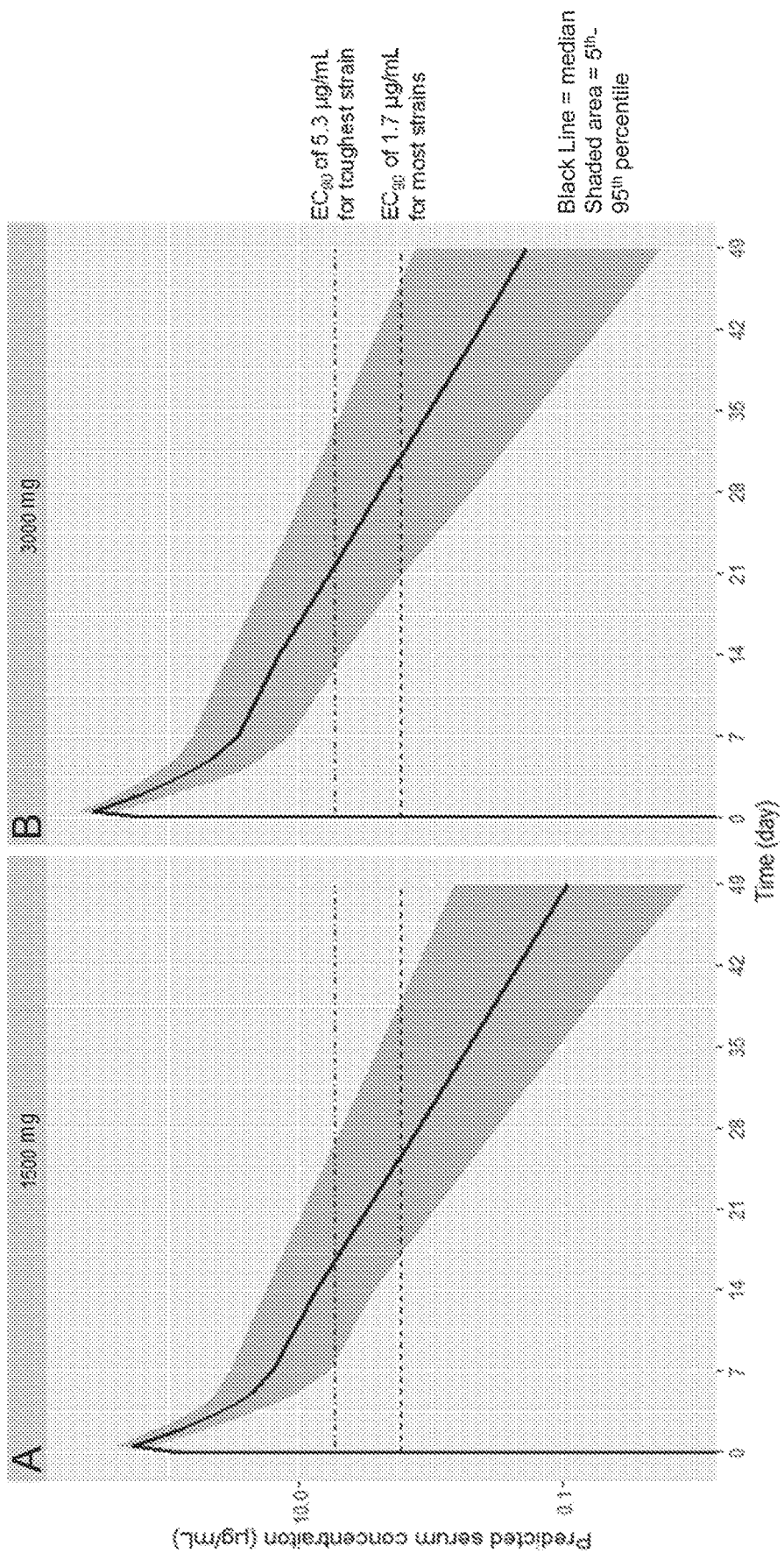

FIG. 2 Based on observed increased clearance in ICU patients for monoclonal antibodies directed at bacterial pathogens (e.g., MEDI4893), pharmacokinetics were modelled for ICU patients with mechanical ventilation following a single dose of MEDI3902. (A) Single dose of 1500 mg MEDI3902 is predicted to maintain serum exposure at about 1 µg/mL for ≥21 days in >90% subjects. (B) Single dose of 3000 mg MEDI3902 is predicted to maintain serum exposure at about 1.7 µg/mL for ≥21 days in >90% subjects.

Figure 3:
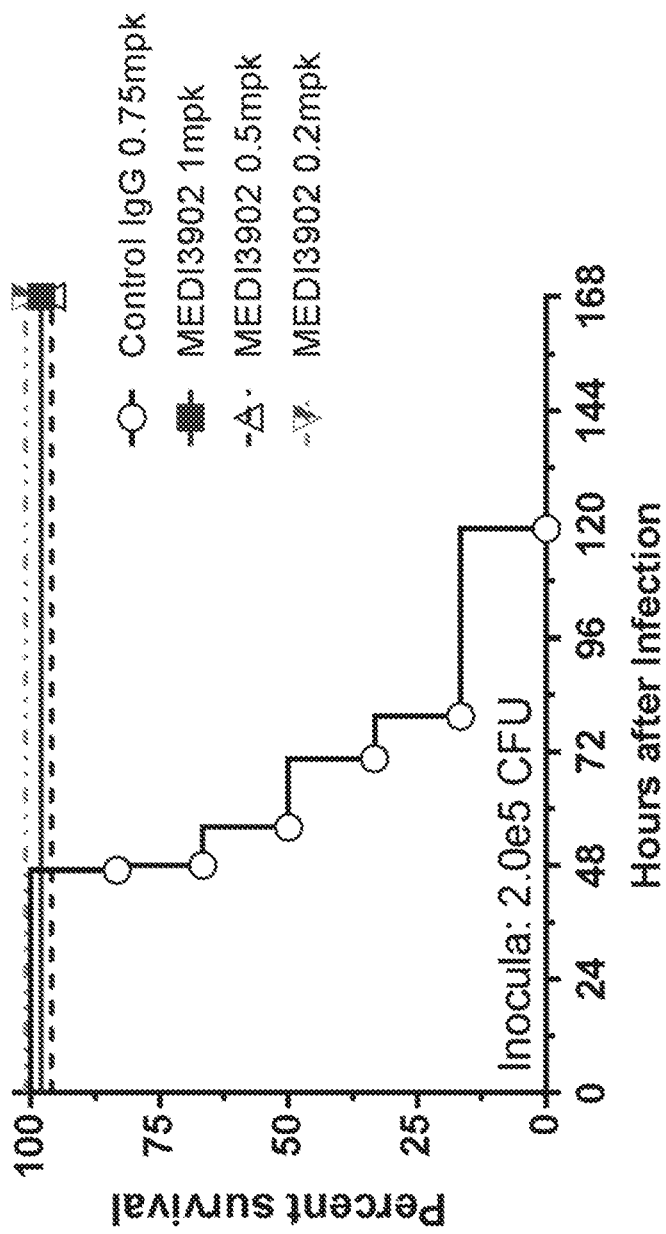

FIG. 3 In vivo survival study of MEDI3902-treated mice in a 6206 acute pneumonia model system. Mice (n=6) were treated with an isotype control IgG (negative control, 0.75 mg/kg) or MEDI3902 at three doses: 1 mg/kg, 0.5 mg/kg, or 0.2 mg/kg. Twenty-four hours post-treatment, all mice were infected with ~2×10$^5$ CFU/animal of *P. aeruginosa* stain 6206. All mice were monitored for 168 hours. All of the control mice succumbed to infection by approximately 120 hours post-infection. All of the MEDI3902-treated animals survived. Results are represented as Kaplan-Meier survival curves.

DETAILED DESCRIPTION

Abbreviations

Abbreviations used in this disclosure are listed in Table 1.

TABLE 1

Abbreviations

| Abbreviation or Specialized Term | Definition |
|---|---|
| ADA | anti-drug antibody |
| AE | adverse event |
| AESI | adverse event of special interest |
| APACHE-II | Acute Physiology and Chronic Health Evaluation-II |
| AUC | area under concentration time curve |
| $AUC_\infty$ | area under the concentration-time curve from time zero to infinity |
| $AUC_{Day\ 22-Day\ 29}$ | area under the concentration time curve from day 22 to day 29 |
| BAL | bronchoalveolar lavage |
| $C_{max}$ | mean observed maximum concentration |
| CPIS | Clinical Pulmonary Infection Score |
| $EC_{90}$ | effective serum concentration associated with 90% survival |
| $FiO_2$ | fraction of inspired oxygen |
| ICU | intensive care unit |
| Ig | immunoglobulin |
| IgG1 | immunoglobulin G1 |
| IL | interleukin |
| ITT | intent-to-treat |
| IV | intravenous |
| LLOQ | lower limit of quantification |
| mAb | monoclonal antibody |
| $O_2$ | oxygen |
| OPK | opsonophagocytic killing |
| *P. aeruginosa* | *Pseudomonas aeruginosa* |
| $PaO_2$ | partial pressure of oxygen |
| PCR | polymerase chain reaction |
| PD | pharmacodynamic |
| PK | pharmacokinetics |
| RBC | red blood cell |
| SAE | serious adverse event |
| SOFA | Sequential Organ Failure Assessment |
| TEAE | treatment-emergent adverse event |
| TESAE | treatment-emergent serious adverse event |
| VAP | ventilator-associated pneumonia |
| $Vd_{ss}$ | volume of distribution at steady state |
| WBC | white blood cell |
| w/v | weight/volume |

Definitions

It is to be noted that the term "a" or "an" entity refers to one or more of that entity; for example, "a binding molecule," is understood to represent one or more binding molecules. As such, the terms "a" (or "an"), "one or more," and "at least one" can be used interchangeably herein.

Furthermore, "and/or" where used herein is to be taken as specific disclosure of each of the two specified features or components with or without the other. Thus, the term and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

Unless defined otherwise, technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry and Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. Unless otherwise indicated, amino acid sequences are written left to right in amino to carboxy orientation. The headings provided herein are not limitations of the various aspects or aspects of the disclosure, which can be had by reference to the specification as a whole. Accordingly, the terms defined immediately below are more fully defined by reference to the specification in its entirety.

Disclosed herein are certain binding molecules, or antigen-binding fragments, variants, or derivatives thereof. Unless specifically referring to full-sized antibodies such as naturally-occurring antibodies, the term "binding molecule" encompasses full-sized antibodies as well as antigen-binding fragments, variants, analogs, or derivatives of such antibodies, e.g., naturally-occurring antibody or immunoglobulin molecules or engineered antibody molecules or fragments that bind antigen in a manner similar to antibody molecules.

As used herein, the term "binding molecule" refers in its broadest sense to a molecule that specifically binds an antigenic determinant. As described further herein, a binding molecule can comprise one or more "binding domains." As used herein, a "binding domain" is a two- or three-dimensional polypeptide structure that can specifically bind a given antigenic determinant, or epitope. A non-limiting example of a binding molecule is a bispecific antibody or fragment thereof that comprises at least two distinct binding domains that specifically bind different antigenic determinants or epitopes. In certain aspects, a bispecific antibody as provided herein can be said to comprise a first binding domain binding to a first epitope, and a second binding domain binding to a second epitope.

The terms "antibody" and "immunoglobulin" can be used interchangeably herein. An antibody (or a fragment, variant, or derivative thereof as disclosed herein comprises at least the variable domain of a heavy chain and at least the variable domains of a heavy chain and a light chain. Basic immunoglobulin structures in vertebrate systems are relatively well understood. See, e.g., Harlow et al., Antibodies: A Laboratory Manual, (Cold Spring Harbor Laboratory Press, 2nd ed. 1988).

As will be discussed in more detail below, the term "immunoglobulin" comprises various broad classes of polypeptides that can be distinguished biochemically. Those skilled in the art will appreciate that heavy chains are classified as gamma, mu, alpha, delta, or epsilon (γ, μ, α, δ, ε) with some subclasses among them (e.g., γ1-γ4). It is the nature of this chain that determines the "class" of the antibody as IgG, IgM, IgA IgG, or IgE, respectively. The immunoglobulin subclasses (isotypes) e.g., $IgG_1$, $IgG_2$, $IgG_3$, $IgG_4$, $IgA_1$, etc. are well characterized and are known to confer functional specialization. Modified versions of each of these classes and isotypes are readily discernible to the skilled artisan in view of the instant disclosure and, accordingly, are within the scope of this disclosure.

Light chains are classified as either kappa or lambda (κ, λ). Each heavy chain class can be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain.

Both the light and heavy chains are divided into regions of structural and functional homology. The terms "constant" and "variable" are used functionally. In this regard, it will be appreciated that the variable domains of both the light (VL) and heavy (VH) chain portions determine antigen recognition and specificity. Conversely, the constant domains of the light chain (CL) and the heavy chain (CH1, CH2 or CH3) confer important biological properties such as secretion, transplacental mobility, Fc receptor binding, complement binding, and the like. By convention the numbering of the constant region domains increases as they become more distal from the antigen binding site or amino-terminus of the antibody. The N-terminal portion is a variable region and at the C-terminal portion is a constant region; the CH3 and CL domains actually comprise the carboxy-terminus of the heavy and light chain, respectively.

As indicated above, the variable region allows the binding molecule to selectively recognize and specifically bind epitopes on antigens. That is, the VL domain and VH domain, or subset of the complementarity determining regions (CDRs), of a binding molecule, e.g., an antibody combine to form the variable region that defers a three dimensional antigen binding site. This quaternary binding molecule structure forms the antigen binding site present at the end of each arm of the Y. More specifically, the antigen binding site is defined by three CDRs on each of the VH and VL chains.

In naturally occurring antibodies, the six "complementarity determining regions" or "CDRs" present in each antigen binding domain are short, non-contiguous sequences of amino acids that are specifically positioned to form the antigen binding domain as the antibody assumes its three dimensional configuration in an aqueous environment. The remainder of the amino acids in the antigen binding domains, referred to as "framework" regions, show less inter-molecular variability. The framework regions largely adopt a β-sheet conformation and the CDRs form loops that connect, and in some cases form part of, the β-sheet structure. Thus, the framework regions act to form a scaffold that provides for positioning the CDRs in correct orientation by inter-chain, non-covalent interactions. The antigen binding domain formed by the positioned CDRs defines a surface complementary to the epitope on the immunoreactive antigen. This complementary surface promotes the non-covalent binding of the antibody to its cognate epitope. The amino acids comprising the CDRs and the framework regions, respectively, can be readily identified for any given heavy or light chain variable region by one of ordinary skill in the art, since they have been precisely defined (see, "Sequences of Proteins of Immunological Interest," Kabat, E., et al., U.S. Department of Health and Hyman Services, (1983); and Chothia and Lesk, *J. Mol. Biol.*, 196:901-917 (1987), which are incorporated herein by reference in their entireties).

Antibodies or antigen-binding fragments, variants, or derivatives thereof include, but are not limited tomonoclonal, human, humanized, or chimeric antibodies, single chain Fvs (scFv), and multispecific antibodies, e.g., bispecific antibodies. ScFv molecules are known in the art and are described, e.g., in U.S. Pat. No. 5,892,019. Immunoglobulin or antibody molecules encompassed by this disclosure can be of any type (e.g., IgG, IgE, IgM, IgD, IgA, and IgY), class (e.g., IgG1, IgG2, IgG3, IgG4, IgA1 and IgA2) or subclass of immunoglobulin molecule.

By "specifically binds," it is generally meant that a binding molecule, e.g., a bispecific antibody or fragment, variant, or derivative thereof binds to an epitope via an antigen binding domain, and that the binding entails some complementarity between an antigen binding domain and the epitope. A binding molecule as provided herein can contain one, two, three, four, or more binding domains that can be the same or different, and that can bind to the same epitope, or to two or more different epitopes. According to this definition, a binding molecule is said to "specifically bind" to an epitope when it binds to that epitope, via its antigen binding domain more readily than it would bind to a random, unrelated epitope. The term "specificity" is used herein to qualify the relative affinity be which a certain binding molecule binds to a certain epitope. For example, binding molecule "A" may be deemed to have a higher specificity for a given epitope than binding molecule "B," or binding molecule "A" may be said to bind to epitope "C" with a higher specificity than it has for related epitope "D."

Antibody fragments including single-chain antibodies can comprise the variable region(s) alone or in combination with the entirety or a portion of the following: hinge region, CH1, CH2, and CH3 domains. Also included are antigen-binding fragments also comprising any combination of variable region(s) with a hinge region, CH1, CH2, and CH3 domains. Antibodies, or antigen-binding fragments thereof disclosed herein can be from any animal origin including birds and mammals. The antibodies can be human murine donkey rabbit, goat, guinea pig, camel, llama, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins and that do not express endogenous immunoglobulins, as described infra and, for example in, U.S. Pat. No. 5,939,598 by Kucherlapati et al.

As used herein, the term "light chain portion" includes amino acid sequences derived from an immunoglobulin light chain. The light chain portion comprises at least one of a VL or CL domain.

The term "multispecific antibody" or "bispecific antibody" as used herein refer to an antibody that has binding domains specific for two or more different antigens or epitopes within a single antibody molecule. It will be appreciated that other molecules in addition to the canonical antibody structure can be constructed with two binding specificities. It will further be appreciated that antigen binding by bispecific antibodies can be simultaneous or sequential. Triomas and hybrid hybridomas are two examples of cell lines that can secrete bispecific antibodies. Bispecific antibodies can also be constructed by recombinant means, (Ströhlein and Heiss, *Future Oncol.* 6:1387-94 (2010); Mabry and Snavely, *IDrugs,* 13:543-9 (2010)).

As used herein, the term "engineered antibody" refers to an antibody in which the variable domain in either the heavy and light chain or both is altered by at least partial replacement of one or more CDRs from an antibody of known specificity and, if necessary, by partial framework region replacement and sequence changing. Although the CDRs can be derived from an antibody of the same class or even subclass as the antibody from which the framework regions are derived, it is envisaged that the CDRs will be derived from an antibody of different class and preferably from an antibody from a different species. An engineered antibody in which one or more "donor" CDRs from a non-human antibody of known specificity is grafted into a human heavy or light chain framework region is referred to herein as a "humanized antibody." It may not be necessary to replace all of the CDRs with the complete CDRs from the donor variable region to transfer the antigen binding capacity of one variable domain to another. Rather, it may only be necessary to transfer those residues that are necessary to maintain the activity of the target binding site. Given the explanations set forth in, e.g., U.S. Pat. Nos. 5,585,089, 5,693,761, 5,693,762, and 6,180,370, it will be well within the competence of those skilled in the art, either by carrying out routine experimentation or by trial and error testing to obtain a functional engineered or humanized antibody.

As used herein, the terms "treat" or "treatment" refers to therapeutic treatment, wherein the object is to clear or reduce the bacterial burden of an infectious agent in a subject that has been clinically diagnosed with an infection, such as pneumonia, bacteremia, peritonitis, sepsis, and/or an abscess. "Treatment" can also mean prolonging survival as compared to expected survival if not receiving treatment. Those in need of treatment include those already with the infection, condition, or disorder as well as those prone to base the condition or disorder or those in which the condition or disorder is to be prevented, e.g., in burn patients or immunosuppressed patients susceptible to bacterial infection, e.g., *P. aeruginosa* infection.

As used herein, the terms "prevent" or "mitigate" refer to prophylactic or preventative measures, wherein the object is to prevent or slow down (lessen) an undesired physiological change, infection, or disorder. Beneficial or desired clinical results include, but are not limited to, alleviation of symptoms, diminishment of extent of disease, stabilized (i.e., not worsening) state of disease, clearance or reduction of an infectious agent such as *P. aeruginosa* in a subject, a delay or slowing of disease progression, amelioration or palliation of the disease state, and remission (whether partial or total), whether detectable or undetectable.

As used herein, the terms "nosocomial disease" and "nosocomial infection" refer to a disease or infection occurring or originating in a hospital or other healthcare facility. Nosocomial infections are typically infections that are contracted in a hospital or other healthcare facility, and can be caused by infectious agents, e.g., bacteria that are resistant to antibiotics. In certain aspects, a nosocomial infection is not present or incubating prior to the subject being admitted to the hospital or healthcare facility, which is acquired or contracted after the subject's admittance to the hospital or healthcare facility.

Similarly, an "iatrogenic disease" or "iatrogenic infection" is one that is caused by or occurs as a result of medical care.

By "subject" or "individual" or "animal" or "patient" or "mammal," is meant any subject, e.g., a mammalian subject, for whom diagnosis, prognosis, or therapy is desired. Mammalian subjects include humans, domestic animals, farm animals, and zoo, sports, or pet animals such as dogs, cats, guinea pigs, rabbits, rats, mice, horses, cattle, cows, bears, and so on.

As used herein, phrases such as "a subject that would benefit from administration of an anti-*Pseudomonas aeruginosa* Psl and PcrV bispecific binding molecule" and "an animal in need of treatment" includes subject, such as mammalian subjects, that would benefit from administration of an anti-*Pseudomonas* Psl and PcrV bispecific binding molecule, such as a bispecific antibody. Such binding molecules can be used, e.g., for detection of *Pseudomonas* Psl or PcrV (e.g., for a diagnostic procedure) and/or for treatment, i.e., palliation or prevention of a disease, with anti-*Pseudomonas aeruginosa* Psl and PcrV bispecific binding molecules. As described in more detail herein, the anti-*Pseudomonas aeruginosa* Psl and PcrV bispecific binding molecules can be used in unconjugated form or can be conjugated, e.g., to a drug, prodrug, or an isotope.

As used herein the terms "susceptible subject" or "susceptible human subject" refer to a subject, e.g., a human patient, who is at risk, e.g., low risk, moderate risk, or high risk, of contacting a disease, e.g., a disease associated with *P. aeruginosa*, because of prior or current injury or disease, planned, current, or prior hospitalization, e.g., in an intensive care unit, assisted breathing, e.g., via mechanical ventilation through intubation or a tracheostomy, and/or known colonization with *P. aeruginosa*, e.g., in the respiratory tract, where the *P. aeruginosa* can be, in some instances, antibiotic resistant. In certain aspects a subject colonized with *P. aeruginosa* can be symptom-free, or can exhibit mild, moderate, or severe disease symptoms, e.g., pneumonia symptoms as described elsewhere herein. A prior or current infection can be, e.g., a burn infection, a joint infection, a wound infection, a skin infection, an intra-abdominal infection, bacteremia, peritonitis, sepsis, an abscess, a bone infection, or a combination of two or more such infections. In certain aspects the subject can have, or be at risk of contracting acute pneumonia, burn injury, corneal infection, fibrosis, or a combination thereof. In certain aspects, a susceptible human subject can be treated with a bispecific antibody as provided herein to prevent disease, e.g., nosocomial disease, iatrogenic disease, or a disease caused by *P. aeruginosa*, from occurring, or to mitigate, e.g., alleviate, reduce, diminish, lessen, weaken, lighten, attenuate, palliate, or relieve, disease or infection symptoms resulting from *P. aeruginosa* infection, or to treat an infection resulting from *P. aeruginosa*, e.g., eliminating or lowering the bacterial burden of a *P. aeruginosa* infection. In certain aspects a susceptible human subject is a subject in need of treatment, e.g., based on risk factors (as noted above) for contracting a disease treatable by the methods provided herein, or because of existing symptoms that require treatment.

Bispecific Antibodies

The methods provided by this disclosure utilize bispecific antibodies or antigen-binding fragments thereof, which specifically bind to *Pseudomonas aeruginosa* Psl and PcrV. The bispecific antibodies or fragments thereof as disclosed herein comprise polypeptides, e.g., amino acid sequences encoding, for example, Psl-specific and PcrV-specific antigen binding regions derived from immunoglobulin molecules. A polypeptide or amino acid sequence "derived from" a designated protein refers to the origin of the polypeptide. In certain cases, the polypeptide or amino acid sequence that is derived from a particular starting polypeptide or amino acid sequence has an amino acid sequence that is essentially identical to that of the starting sequence, or a portion thereof, wherein the portion consists of at least 10-20 amino acids, at least 20-30 amino acids, at lease 30-50 amino acids, or that is otherwise identifiable to one of ordinary skill in the art as having its origin in the starting sequence.

Exemplary bispecific antibodies for use in the methods provided herein are disclosed, e.g., in PCT Publication No. WO 2013/070615, PCT Publication No. WO 2014/074528, PCT Application No. PCT/US2015/029063, and PCT Application No. PCT/US2015/036576, the disclosures of which are incorporated by reference herein in their entireties.

Exemplary portions of a bispecific antibody for use in the methods provided herein are presented in Table 2. The CDRs in the VH, VL, and scFv sequences are underlined. The linker sequences are double underlined.

TABLE 2

Sequences

| SEQ ID NO: | Description | Amino Acid Sequence |
|---|---|---|
| 1 | Anti-PcrV VH | EVQLLESGGG LVQPGGSLRL SCAASGFTFS SYAMNWVRQA PGKGLEWVS AITMSGITAYY TDDVKGRFTI SRDNSKNTLY LQMNSLRAED TAVYYCAKEE FLPGTHYYYG MDVWGQGTTV TVSS |
| 2 | HCDR1-PcrV | SYAMN |
| 3 | HCDR2-PcrV | AITMSGITAYYTDDVKG |
| 4 | HCDR3-PcrV | EEFLPGTHYYYGMDV |
| 5 | Anti-PcrV VL | AIQMTQSPSS LSASVGDRVT ITCRASQGIR NDLGWYQQKP GKAPKLLIYS ASTLQSGVPS RFSGSGSGTD FTLTISSLQP EDFATYYCLQ DYNYPWTFGQ GTKVEIK |
| 6 | LCDR1-PcrV | RASQGIRNDLG |
| 7 | LCDR2-PcrV | SASTLQS |
| 8 | LCDR3-PcrV | LQDYNYPWT |
| 9 | Anti-Psl scFv | QVQ LQESGPGLVK PSETLSLTCT VSGGSISPYY WTWIRQPPGK CLELIGYIHS SGYTDYNPSL KSRVTISGDT SKKQFSLKLS SVTAADTAVY YCARADWDRL RALDIWGQGT MVTVSSGGGG SGGGGSGGGG SGGGGSDIQL TQSPSSLSAS VGDRVIITCR ASQSIRSHLN WYQQKPGKAP KLLIYGASNL QSGVPSRFSG SGSGTDFTLT ISSLQPEDFA TYYCQQSTGA WNWFGCGTKV EIK |
| 10 | HCDR1-Psl | PYYWT |
| 11 | HCDR2-Psl | YIHSSGYTDYNPSLKS |
| 12 | HCDR3-Psl | ADWDRLRALDI |
| 13 | LCDR1-Psl | RASQSIRSHLN |
| 14 | LCDR2-Psl | GASNLQS |
| 15 | LCDR3-Psl | QQSTGAWNW |
| 16 | CH1 | ASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK RV |
| 17 | H1 | EPKSC |
| 18 | H2 | DKTHTCPPCP |
| 19 | CH2-CH3 | APELLGGPSVFLFPPKPKDTLX$_1$IX$_2$RX$_3$PEVTCVVV DVSHEDPEVKFNWYVDGVEVHNAKTKPREEQYNSTY RVVSVLTVLHQDWLNGKEYKCKVSNKALPAPIEKTI SKAKGQPREPQVYTLPPSREEMTKNQVSLTCLVKGF YPSDIAVEWESNGQPENNYKTTPPSLDSDGSFFLYS KLTVDKSRWQQGNVFSCSVMHEALHNHYTQKSLSLS PGK, wherein X$_1$ is M or Y, X$_2$ is S or T, and X$_3$ is T or E |
| 20 | CH2-CH3 | APELLGG PSVFLFPPKP KDTLMISRTP EVTCVVVDVS HEDPEVKFNWYVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNEQPENNYKTTPPV LDSDGSFFLY SKLTVDKSRW QQGNVFSCSV MHEALHNHYT QKSLSLSPGK |
| 21 | MEDI3902 Heavy Chain | EVQLLESGGG LVQPGGSLRL SCAASGFTFS SYAMNWVRQA PGKGLEWVS AITMSGITAYY TDDVKGRFTI SRDNSKNTLY LQMNSLRAED TAVYYCAKEE FLPGTHYYYG MDVWGQGTTV TVSS ASTKGP SVFPLAPSSK STSGGTAALG CLVKDYFPEP VTVSWNSGAL TSGVHTFPAV LQSSGLYSLS SVVTVPSSSL GTQTYICNVN HKPSNTKVDK RVEPKSCGGG GSGGGGS QVQ LQESGPGLVK PSETLSLTCT VSGGSISPYY WTWIRQPPGK CLELIGYIHS SGYTDYNPSL KSRVTISGDT SKKQFSLKLS SVTAADTAVY YCARADWDRL RALDIWGQGT MVTVSSGGGG SGGGGSGGGG SGGGGSDIQL TQSPSSLSAS VGDRVTITCR ASQSIRSHLN WYQQKPGKAP KLLIYGASNL QSGVPSRFSG SGSGTDFTLT ISSLQPEDFA TYYCQQSTGA WNWFGCGTKV EIKGGGGSGG GGSDKTHTCP PCPAPELLGG PSVFLFPPKP KDTLMISRTP EVTCVVVDVS HEDPEVKFNWYVDGVEVHNA KTKPREEQYN STYRVVSVLT VLHQDWLNGK EYKCKVSNKA LPAPIEKTIS KAKGQPREPQ VYTLPPSREE MTKNQVSLTC LVKGFYPSDI AVEWESNGQPENNYKTTPPV LDSDGSFFLY SKLTVDKSRW QQGNVFSCSV MHEALHNHYT QKSLSLSPGK |
| 22 | MEDI3902 Light Chain | AIQMTQSPSS LSASVGDRVT ITCRASQGIR NDLGWYQQKP GKAPKLLIYS ASTLQSGVPS RFSGSGSGTD FTLTISSLQP EDFATYYCLQ DYNYPWTFGQ GTKVEIK RTV AAPSVFIFPP SDEQLKSGTA SVVCLLNNFY PREAKVQWKV DNALQSGNSQ ESVTEQDSKD STYSISSTLT LSKADYEKHK VYACEVTHQG LSSPVTKSFN RGEC |

The bispecific antibody to be administered according to the methods herein includes a binding domain which specifically binds to *P. aeruginosa* Psl comprising a set of complementarity determining regions (CDRs): HCDR1-Psl, HCDR2-Psl, HCDR3-Psl, LCDR1-Psl, LCDR2-Psl, AND LCDR3-Psl, wherein HCDR1-Psl has the amino acid sequence of SEQ ID NO: 10, HCDR2-Psl has the amino acid sequence of SEQ ID NO: 11, HCDR3-Psl has the amino acid sequence of SEQ ID NO: 12, LCDR1-Psl has the amino acid sequence of SEQ ID NO: 13, LCDR2-Psl has the amino acid sequence of SEQ ID NO: 14, and LCDR3-Psl has the amino acid sequence of SEQ ID NO: 15; and a binding domain which specifically binds to *P. aeruginosa* PcrV comprising a set of CDRs: HCDR1-PcrV, HCDR2-PcrV, HCDR3-PcrV, LCDR1-PcrV, LCDR2-PcrV, and LCDR3-PcrV, wherein HCDR1-PcrV has the amino acid sequence of SEQ ID NO: 2, HCDR2-PcrV has the amino acid sequence of SEQ ID NO: 3, HCDR3-PcrV has the amino acid sequence of SEQ ID NO: 4, LCDR1-PcrV has the amino acid sequence of SEQ ID NO: 6, LCDR2-PcrV has the amino acid sequence of SEQ ID NO: 7, and LCDR3-PcrV has the amino acid sequence of SEQ ID NO: 8. In embodiments, the bispecific antibody has a heavy chain and a light chain. The heavy chain includes the formula VH-CH1-H1-L1-S-L2-H2-CH2-CH3, where VH is an anti-*P. aeruginosa* PcrV heavy chain variable domain including the amino acid sequence of SEQ ID NO: 1. CH1 is a heavy chain constant region domain-1, H1 is a first heavy chain hinge region fragment, L1 is a first linker, S is an anti-*P. aeruginosa* Psl ScFv molecule including the amino acid sequence of SEQ ID NO: 9, L2 is a second linker, H2 is a second heavy chain hinge region fragment CH2 is a heavy chain constant region domain-2, and CH3 is a heavy chain constant legion domain-3. The light chain includes the formula VL-CL, where VL is an anti-*P. aeruginosa* PcrV light chain variable domain including the amino acid sequence of SEQ ID NO: 5 and CL includes an antibody light chain kappa constant region or an antibody light chain lambda region. In certain aspects, CH1 can include the amino acid sequence of SEQ ID NO: 16. In certain aspects L1 and L2 can be the same or different, and can independently include (a) [GGGGS]n, where n is 0, 1, 2, 3, 4, or 5 (SEQ ID NO: 23). (b) [GGGG]n, where n is 0, 1, 2, 3, 4, or 5 (SEQ ID NO: 24), or a combination of (a) and (b). In certain aspects, H1 can include the amino acid sequence EPKSC (SEQ ID NO: 17). In certain aspects, H2 can include the amino acid sequence DKTHTCPPCP (SEQ ID NO: 18). In certain aspects, CH2-CH3 can include the amino acid sequence of SEQ ID NO: 19. In certain aspects CH2-CH3 can include the amino acid sequence of SEQ ID NO: 20. In certain aspects, the heavy chain of the bispecific antibody can include the amino acid sequence of SEQ ID NO: 21, and the light chain includes the amino acid sequence of SEQ ID NO: 22.

Pharmaceutical Compositions Comprising Anti-*Pseudomonas aeruginosa* Psl and PcrV Bispecific Binding Molecules Pharmaceutical compositions used in this disclosure comprise pharmaceutically acceptable carriers well known to those of ordinary skill in the art. Preparations for parenteral administration include sterile aqueous or non-aqueous solutions, suspensions, and emulsions.

The amount of an anti-*Pseudomonas aeruginosa* Psl and PcrV bispecific antibody or fragment, variant or derivative thereof that can be combined with the carrier materials to produce a single dosage form will vary depending upon the subject treated and the particular mode of administration. Exemplary dosage regimens include a single intravenous infusion of an anti-*Pseudomonas aeruginosa* Psl and PcrV bispecific antibody of about 500 to about 3000 mg, e.g., about 500 mg, 600, 700, 750, 1000, 1500 or about 3000 mg. Dosage regimens also can be adjusted to provide the optimum desired response (e.g., a prophylactic response or a therapeutic treatment response).

The route of administration of an anti-*Pseudomonas aeruginosa* Psl and PcrV bispecific antibody or fragment, variant or derivative thereof, can be, for example, parenteral. The term parenteral as used herein includes, e.g., intravenous, intraarterial, intraperitoneal, intramuscular, or subcutaneous administration. A suitable form for administration would be a solution for injection, in particular for intravenous or intraarterial injection or drip.

Anti-*Pseudomonas aeruginosa* Psl and PcrV bispecific antibodies or fragments, variants or derivatives thereof can be administered in a pharmaceutically effective amount for the in vivo treatment of or prevention of *Pseudomonas aeruginosa* infection. In this regard, it will be appreciated that the disclosed binding molecules can be formulated so as to facilitate administration and promote stability of the active agent.

In keeping with the scope of the disclosure, anti-*Pseudomonas aeruginosa* Psl and PcrV bispecific antibodies or fragments, variants or derivatives thereof, can be administered to a human or other animal in accordance with the aforementioned methods of treatment in an amount sufficient to produce a therapeutic effect. The anti-*Pseudomonas aeruginosa* Psl and PcrV bispecific antibodies or fragments, variants or derivatives thereof disclosed herein can be administered to such human or other animal in a conventional dosage form prepared by combining the antibody of the disclosure with a conventional pharmaceutically acceptable carrier or diluent according to known techniques.

Effective doses of the compositions of the present disclosure for treatment of *Pseudomonas aeruginosa* infection vary depending upon many different factors, including means of administration, target site, physiological state of the patient, whether the patient is human or an animal, other medications administered, and whether treatment is prophylactic or therapeutic. Usually, the patient is a human but non-human mammals including transgenic mammals can also be treated. Treatment dosages can be titrated using routine methods known to those of skill in the art to optimize safety and efficacy.

Anti-*Pseudomonas aeruginosa* Psl and PcrV bispecific antibodies or fragments, variants or derivatives thereof can be administered multiple occasions at various frequencies, e.g., as a single dose, depending on various factors known to those of skill in the art.

Methods for Preventing or Treating Nosocomial Infections

This disclosure provides a method of preventing nosocomial infection in a susceptible human subject, where the method includes administering to the subject a dose of about 500 mg to about 3000 mg, e.g., 500 mg, 600 mg, 700 mg, 750 mg, 1000 mg, 1500 mg or 3000 mg, of a bispecific antibody that specifically binds *Pseudomonas aeruginosa* Psl and PcrV. The bispecific antibody can be administered, e.g., as a single dose of about 500 mg to about 3000 mg. e.g., 500 mg, 600 mg, 700 mg, 750 mg, 1000 mg, 1500 mg, or 3000 mg. In certain aspects the bispecific antibody can be administered as an IV infusion. A susceptible human subject, as described in more detail elsewhere herein, is a person who is at risk of contracting a nosocomial infection but at the time of administration does not have an infection or shows no symptoms of an infection; or a person who has contracted a nosocomial infection that requires intervention or mitigation. The method further includes monitoring the subject for symptoms following administration of the bispecific antibody for, e.g., through 1 day, 3 days, 5 days 7 days 10 days, 15 days, 21 days, 28 days, or 30 days. In an embodiment the method includes monitoring the subject for symptoms through at least about 21 days or more from the day of administration. "Nosocomial infections" are defined elsewhere herein and include, e.g., pneumonia, bacteremia, bone infection, joint infection, skin infection, burn infection, wound infection, peritonitis, sepsis, and/or an abscess. Symptoms associated with nosocomial infections, e.g., pneumonia, are known in the art, and exemplary symptoms are described in the Examples below. In certain aspects the nosocomial infection is caused by, or is exacerbated by *P. aeruginosa*. According to this method, the human subject is successfully treated if, e.g., at 1 day, 3 days, 5 days, 8 days, 10 days, 15 days, 21 days, 28 days, or 30 days post-administration, the subject remains symptom-free (if the subject was symptom free at the time of administration) or displays less severe symptoms than would be expected if not treated with MEDI3902. In an embodiment, the human subject is successfully treated if at 21 days post-administration, the subject remains symptom-free (if the subject was symptom free at the time of administration) or displays less severe symptoms than would be expected if not treated with MEDI3902. In another embodiment, the human subject is successfully treated if at 28 or 30 days post-administration, the subject remains symptom-free (if the subject was symptom free at the time of administration) or displays less severe symptoms than would be expected if not treated with MEDI3902.

In another aspect this disclosure provides a method of preventing or treating pneumonia, e.g., hospital acquired or not hospital acquired pneumonia in a susceptible human subject, where the method includes administering to the subject a dose of about 500 mg to about 3000 mg, e.g., 500 mg, 600 mg, 700 mg, 750 mg, 1000 mg, 1500 mg or 3000 mg, of a bispecific antibody that specifically binds *Pseudomonas aeruginosa* Psl and PcrV. The bispecific antibody can be administered e.g., as a single dose of about 500 mg to about 3000 mg, e.g., 500 mg, 600 mg, 700 mg, 750 mg, 1000 mg, 1500 mg or 3000 mg. In certain aspects the bispecific antibody can be administered as an IV infusion. In certain aspects the pneumonia is nosocomial or iatrogenic. A susceptible human subject, as described in more detail elsewhere herein, is a person who is at risk of contracting pneumonia but at the time of administration does not have pneumonia symptoms; or a person who has contracted pneumonia that requires intervention or mitigation. The method further includes monitoring the subject for pneumonia symptoms following administration of the bispecific antibody for, e.g., through 1 day, 3 days, 5 days, 8 days, 10 days, 15 days, 21 days, 28 days, or 30 days. In an embodiment, the method includes monitoring the subject for symptoms at least about 21 days from the day of administration. Symptoms associated with pneumonia are known in the art, and exemplary symptoms are described in the Examples below. In certain aspects the pneumonia is caused by, or is exacerbated by, *P. aeruginosa*. According to this method, the human subject is successfully treated if, e.g., at 1 day, 3 days, 5 days, 8 days, 10 days, 15 days, 21 days, 28 days, or 30 days post-administration, the subject remains symptom-free (if the subject was symptom free at the time of administration) or displays less severe symptoms than would be expected if not treated with MEDI3902. In an embodiment, the human subject is successfully treated if at 7 days post-administration, the subject remains symptom-free (if the subject was symptom-free at the time of administration) or displays less severe symptoms than would be expected if not treated with MEDI3902. In an embodiment, the human subject is successfully treated if at 7 days post-administration, the subject remains symptom-free (if the subject was symptom-free at the time of administration) or displays less severe symptoms than would be expected if not treated with MEDI3902. In an embodiment, the human subject is successfully treated if at 21 days post-administration, the subject remains symptom-free (if the subject was symptom-free at the time of administration) or displays less severe symptoms than would be expected if not treated MEDI3902. In an embodiment, the human subject is successfully treated if at 28 or 30 days post-administration, the subject remains symptom-free (if the subject was symptom-free at the time of administration) or displays less severe symptoms than would be expected if not treated with MEDI3902.

In another aspect this disclosure prides a method of preventing or treating a disease caused by *Pseudomonas aeruginosa* e.g., pneumonia, tracheobronchitis, bacteremia, endocarditis, meningitis, otitis media bacterial keratitis, endophthalmitis, osteomyelitis, gastrointestinal disease, skin infection, septicemia, or any combination thereof, in a susceptible human subject, where the method includes administering to the subject a dose of about 500 mg to about 3000 mg, e.g., 500 mg, 600 mg, 700 mg, 750 mg, 1000 mg, 1500 mg, or 3000 mg, of a bispecific antibody that specifically binds *Pseudomonas aeruginosa* Psl and PcrV. The bispecific antibody can be administered, e.g., as a single dose of about 500 mg, to about 3000 mg. e.g., 500 mg, 600 mg, 700 mg, 750 mg, 1000 mg, 1500 mg m 3000 mg. In certain aspects the bispecific antibody can be administered as an IV infusion. In certain aspects the disease caused by *Pseudomonas aeruginosa* is nosocomial or iatrogenic. A susceptible human subject, as described in more detail elsewhere herein, is a person who is at risk of contracting a disease treatable or preventable by the methods provided herein but at the time of administration does not have disease symptoms; or a person who has contracted disease caused by *Pseudomonas aeruginosa* that requires treatment, intervention or mitigation. The method further includes monitoring the subject for disease symptoms following administration of the bispecific antibody through e.g., 1 day, 3 days, 5 days, 8 days, 10 days, 15 days, 21 days, 28 days, or 30 days. In an embodiment, the method includes monitoring the subject for symptoms through at least about 21 days from the day of administration. Symptoms associated with pneumonia are known in the art, and exemplary symptoms are described in the Examples below. According to this method the human subject is successfully treated if, e.g., at 1 day, 3 days, 5 days, 8 days, 10 days, 15 days, 21 days, 28 days, or 30 days post-administration, the subject remains symptom-free (if the subject was symptom free at the time of administration) or displays less severe symptoms than would be expected if not treated with MEDI3902. In an embodiment, the human subject is successfully treated if at 7 days post-administration, the subject remains symptom-free (if the subject was symptom-free at the time of administration) or displays less severe symptoms than would be expected if not treated with MEDI3902. In an embodiment, the human subject is successfully treated if at 21 days post-administration, the subject remains symptom-free (if the subject was symptom free at the time of administration) or displays less severe symptoms than would be expected if not treated with MEDI3902. In another embodiment, the human subject is successfully treated if at 28 or 30 days post-administration, the subject remains symptom-free (if the subject was symptom free at the time of administration) or displays less severe symptoms than would be expected if not treated with MEDI3902.

In certain aspects the bispecific antibody to be administered according to the methods herein includes a binding domain which specifically binds to Psl comprising a set of Complementarity-Determining Regions (CDRs): HCDR1-Psl, HCDR2-Psl, HCDR3-Psl, LCDR1-Psl, LCDR2-Psl, and LCDR3-Psl, wherein HCDR1-Psl has the amino acid sequence of SEQ ID NO: 10. HCDR2-Psl has the amino acid sequence of SEQ ID NO: 11, HCDR3-Psl has the amino acid sequence of SEQ ID NO: 12, LCDR1-Psl has the amino acid sequence of SEQ ID NO: 13, LCDR2-Psl has the amino acid sequence of SEQ ID NO: 14, and LCDR3-Psl has the amino acid sequence of SEQ ID NO: 15; and a binding domain which specifically binds to PcrV comprising HCDR1-PcrV, HCDR2-PcrV, HCDR3-PcrV, LCDR1-PcrV, LCDR2-PcrV, and LCDR3-PcrV, wherein HCDR1-PcrV has the amino acid sequence of SEQ ID NO: 2, HCDR2-PcrV has the amino acid sequence of SEQ ID NO: 3 HCDR3-PcrV has the amino acid sequence of SEQ ID NO: 4, LCDR1-PcrV has the amino acid sequence of SEQ ID NO: 6, LCDR2-PcrV has the amino acid sequence of SEQ ID NO: 7, and LCDR3-PcrV has the amino acid sequence of SEQ ID NO. 8. In embodiments, the bispecific antibody has a heavy chain and a light chain. The heavy chain includes the formula VH-CH1-H1-L1-S-L2-H2-CH2-CH3, where VH is an anti-PcrV heavy chain satiable domain including the amino acid sequence of SEQ ID NO: 1, CH1 is a heavy chain constant region domain-1, H1 is a first heavy chain hinge region fragment, L1 is a first linker, S is an anti-Psl ScFv molecule including the amino acid sequence of SEQ ID NO: 9, L2 is a second linker, H2 is a second heavy chain hinge region fragment, CH2 is a heavy chain constant region domain-2, and CH3 is a heavy chain constant region domain-3. The light chain includes the formula VL-CL, where VL is an anti-PcrV light chain variable domain including the amino acid sequence of SEQ ID NO: 5 and CL includes an antibody light chain kappa constant region or an antibody light chain lambda region. In certain aspects, CH1 can include the amino acid sequence of SEQ ID NO: 16. In certain aspects L1 and L2 can be the same or different, and can independently include (a) [GGGGS]n, where n is 0, 1, 2, 3, 4, or 5 (SEQ ID NO: 23), (b) [GGGG]n, where n is 0, 1, 2, 3, 4, or 5 (SEQ ID NO: 24), or a combination of (a) and (b). In certain aspects, H1 can include the amino acid sequence EPKSC (SEQ ID NO: 17). In certain aspects, H2 can include the amino acid sequence DKTHTCPPCP (SEQ ID NO: 18). In certain aspects, CH2-CH3 can include the amino acid sequence of SEQ ID NO: 19. In certain aspects CH2-CH3 can include the amino acid sequence of SEQ ID NO: 20. In certain aspects, the heavy chain of the bispecific antibody can include the amino acid sequence of SEQ ID NO: 21, and the light chain includes the amino acid sequence of SEQ ID NO: 22.

The bispecific antibody for use in the method provided herein can be administered, e.g., as a single dose of about 500 mg to about 3000 mg e.g., 500 mg, 600 mg, 700 mg, 750 mg, 1000 mg, 1500 mg, or 3000 mg.

In some embodiments, the serum target level of the bispecific antibody or antigen-binding fragments thereof is in the range of about 1 µg/mL to about 10 µg/mL, about 2 µg/mL to about 9 µg/mL, about 3 µg/mL to about 8 µg/mL, about 4 µg/mL to about 7 µg/mL, about 5 µg/mL to about 6 µg/mL, about 5 µg/mL to about 7 µg/mL, 5 µg/mL to about 8 µg/mL, 5 µg/mL to about 9 µg/mL, or about 5 µg/mL to about 10 µg/mL. In other embodiments, the serum target level of the bispecific antibody or antigen-binding fragment thereof is in the range of about 1 µg/mL to about 6 µg/mL, about 1 µg/mL to about 5 µg/mL, about 1 µg/mL to about 4 µg/mL, about 1 µg/mL to about 3 µg/mL, or about 1 µg/mL to about 2 µg/mL. In one embodiment, the serum target level of the bispecific antibody or antigen binding fragments thereof is at least 1.7 µg/mL. In another embodiment the serum target level of the bispecific antibody or antigen-binding fragments thereof is at least 5.3 µg/mL. A serum target level of about 1.7 µg/mL is expected to prevent or treat infections caused by >80-90% of *P. aeruginosa* stains. A serum target level of about 5.3 µg/mL is expected to prevent or treat infections caused by the toughest *P. aeruginosa* strains (e.g., those strains that are highly virulent and resistant to antibiotics, such as ARC3928 and ARC3502).

In certain aspects the bispecific antibody for use in the methods provided herein can be administered as an IV infusion.

The methods provided herein are suitable for use with susceptible human subjects as described elsewhere herein. Examples include subjects who are about to be hospitalized, are currently hospitalized, were recently hospitalized, are about to be, currently, or recently on a mechanical ventilator, or a combination thereof. Hospitalization, in some instances, can be in an intensive care unit (ICU). Mechanical ventilation, if required, can be through intubation, e.g., through an endotracheal or nasotracheal tube, or through a tracheostomy. Patients who are about to be, are currently, or were recently on mechanical ventilation can have a heightened risk of contracting a respiratory infection, e.g., pneumonia, e.g., *Pseudomonas aeruginosa* pneumonia. In those situations where mechanical ventilation is indicated, administration of a bispecific antibody as provided by the disclosed methods can reduce the risk of contracting pneumonia, for example, while currently on mechanical ventilation, after mechanical ventilation is no longer required, or a combination thereof.

In certain aspects the subject is colonized with *Pseudomonas aeruginosa* in the respiratory tract, e.g., the lower respiratory tract, at the time of administration of the bispecific antibody. In certain aspects the subject's respiratory tract is colonized with *P. aeruginosa* one, two, three, or four days prior to administration of the bispecific antibody. Colonization can be measured, e.g., by detection of *P. aeruginosa* in a tracheal aspirate within 6 hours, 12 hours, 24 hours, 48 hours, 72 hours, or 96 hours prior to administration of the bispecific antibody. In certain aspects of the methods provided herein, the subject has not received antibiotics considered active against the *P. aeruginosa* strain with which the subject is colonized prior to administration of the bispecific antibody. In certain aspects, the subject's respiratory tract can be additionally colonized by *Staphylococcus aureus* at the time of administration of the bispecific antibody.

In certain aspects the subject does not have pneumonia symptoms at the time of administration of the bispecific antibody. Symptoms can be measured according to the Clinical Pulmonary Infection Score (CPIS). A lack of symptoms can be inferred e.g., if at 24 hours prior to the administration of the bispecific antibody the subject has a CPIS of less than 6.

The methods provided herein include monitoring a subject for disease symptoms, e.g., pneumonia symptoms, following administration of the bispecific antibody. In certain aspects, the subject can be monitored for pneumonia by chest x-ray, observation of respiratory signs or symptoms of pneumonia, microbiologic confirmation of pneumonia, or any combination thereof. A subject can be determined to have pneumonia, e.g., when a new or worsening infiltrate consistent with pneumonia is observed on a chest x-ray, when the subject displays at least two minor or at least one major respiratory sign or symptoms of pneumonia, when a specimen obtained from the subject is positive for *P. aeruginosa* by culture, or any combination thereof. In certain aspects the specimen is a respiratory secretion of the subject. A respiratory secretion can be obtained from expectorated sputum, by endotracheal aspiration, by bronchoscopy with bronchoalveolar lavage, by use of a protected-specimen brush sampling in an intubated subject, or any combination thereof.

Minor respiratory signs or symptoms of pneumonia include, without limitation, a body temperature of greater than about 38° C., a core body temperature of less than about 35° C. a white blood cell count of greater than about 10,000 cells per cubic millimeter ($mm^3$), a white blood cell count of less than about 4,500 cells per $mm^3$, a band neutrophil count of greater than about 15%, production of new purulent endotracheal secretions or sputum, new auscultatory findings, dullness to percussion, a new onset of cough, dyspnea, tachypnea, hypoxemia, or any combination thereof. Major respiratory signs or symptoms of pneumonia can include, without limitation, an acute change made in the ventilatory support system to enhance oxygenation comprising a $PaO_2/FiO_2$ ratio less than about 240 mm Hg maintained for at least four hours, a decrease in the $PaO_2/FiO_2$ ratio of greater than about 50 mm Hg maintained for at least four hours, the necessity to initiate or reinitiate mechanical ventilation in a non-mechanically ventilated subject, or any combination thereof. Microbiologic confirmation of pneumonia can include, without limitation, a respiratory specimen positive for *P. aeruginosa* by culture, a blood culture positive for *P. aeruginosa*, a pleural fluid aspirate or lung tissue culture positive for *P. aeruginosa*, or any combination thereof.

In certain aspects, the methods provided by this disclosure can further include administering an antibiotic to the subject prior to, concurrently with, and/or following administration of the bispecific antibody. Suitable antibiotics can include, without limitation, aminoglycosides, ticarcillin, ureidopenicillins, ciprofloxacin, cefepime, gentamicin, amikacin, tobramycin, ceftazidime, aztreonam, cefotaxime, or any combination thereof. Suitable dosages and length of treatment can be readily determined by a healthcare provider. In certain aspects, the *P. aeruginosa* strain with which the subject is colonized is sensitive to the antibiotic chosen for administration. In other aspects, however, the *P. aeruginosa* strain with which the subject is colonized is resistant or partially resistant to one or more of the available antibiotics chosen for administration. In preclinical studies, for example, MEDI3902 has shown synergistic enhancement of antibiotic therapy against *P. aeruginosa* pneumonia with distinct antibiotic classes against both antibiotic-sensitive and antibiotic-resistant *P. aeruginosa*.

In certain aspects, the methods provided by this disclosure can further include administering an antihistamine to the subject prior to, concurrently with, and/or following administration of the bispecific antibody. Suitable antihistamines can include, without limitation, diphenhydramine, clemastine, dexchlorpheniramine, azelastine, cetirizine, desloratadine, fexofenadine, levocetirizine, loratadine, olopatadine, or any combination thereof. Suitable dosages and length of treatment can be readily determined in a healthcare provider.

In certain aspects, the methods provided by this disclosure include monitoring a subject for serum pharmacokinetics of the bispecific antibody, tracheal secretion pharmacokinetics of the bispecific antibody, or a combination thereof. A subject can maintain, e.g., a serum level of the bispecific antibody of at least about 1 µg/mL, at least about 2 µg/mL, at least about 3 µg/mL, at least about 4 µg/mL, at least about 5 µg/mL, or at least about 5.3 µg/mL or more through day 7, day 14, day 21, day 28, day 30, day 35, day 42, of day 49 following administration of the bispecific antibody. For example, a subject can maintain a serum level of the bispecific antibody of at least about 1.7 µg/mL, or at least about 5.3 µg/mL, or more through day 7, day 14, day 21, day 28, day 30, day 35, day 42, or day 49 following administration of the bispecific antibody. Based on observed increased clearance in ICU patients for monoclonal antibodies directed at bacterial pathogens (e.g., MEDI4893), pharmacokinetics were modelled for ICU patient with mechanical ventilation following a single dose of MEDI3902. A single dose of 1500 mg MEDI3902 is predicted to maintain serum exposure at about 1 µg/mL for ≥21 days in >90% subjects. A single dose of 3000 mg MEDI3902 is predicted to maintain serum exposure at about 1.7 µg/mL for ≥21 days in >90% subjects. Based on pharmacokinetics in healthy volunteers (e.g., without increased clearance like that observed in ICU patients), a single dose of 500 mg, 1500 mg or 3000 mg is expected to maintain serum exposure at about 1 µg/mL for ≥21 days in >90% subjects, for example 1.7 µg/mL for ≥21 days in >90% subjects, such as about 5.3 µg/mL for ≥21 days in >90% subjects. Of course, the serum level of the bispecific antibody will vary throughout the monitoring period, and can reach a maximal concentration of the bispecific antibody, or $C_{max}$, of about 100 µg/mL, about 200 µg/mL, about 300 µg/mL about 400 µg/mL, about 500 µg/mL, or more than about 600 µg/mL, depending on the dose of bispecific antibody administered. In certain aspects, the area under the concentration-time curve from time zero to infinity ($AUC_\infty$) can be measured. For example, the $AUC_\infty$ can be, e.g., about 2000 µg·day/mL to about 6000 µg·day/mL, e.g., about 4000 µg·day/mL for a 1500 mg dose of the bispecific antibody. In certain aspects serum terminal half-life can be measured. In certain aspects the volume of distribution at steady state ($Vd_{ss}$) can be measured. The subject can be monitored for pharmacokinetic parameters through day 7, day 14, day 21, day 28, day 30, day 35, day 42, day 49, or longer following administration of the bispecific antibody. In certain aspects the subject can be monitored through day 21. In certain aspects the subject can be monitored through day 49.

The following disclosed embodiments are merely representative. Thus, specific structural, functional, and procedural details disclosed in the following examples are not to be interpreted as limiting.

EXAMPLES

Example 1

Clinical Trial Phase 1 Study

A Phase 1, first time in human, randomised, double-blind, placebo-controlled, dose-escalation study was conducted that evaluated the safety and tolerability of a single ascending IV dose of MEDI3902 in healthy adult subjects. Adverse event (AE), PK, and ADA data were collected through the last study visit (60 days postdose/Day 61) in the 42 subjects who received MEDI3902 at doses of 250 mg (n=3), 750 mg (n=15), 1500 mg (n=15), or 3000 mg (n=9) and 14 subjects who received placebo. All of the AEs in both the MEDI3902 and placebo groups were either Grade 1 or Grade 2 in severity. The most frequently reported AEs were Grade 1 or Grade 2 infusion-related reactions (15/42 subjects [35.7%] in the total MEDI3902 group; none in the placebo group) and Grade 1 or Grade 2 headache (6/42 subjects [14.3%] in the total MEDI3902 group; 2/14 subjects [14.3%] in the placebo group). Adverse events of special interest (AESIs) included the events of infusion-related reaction (15/42 subjects [35.7%] in the total MEDI3902 group; none in the placebo group), which were mitigated by treatment with diphenhydramine and by slowing the infusion rate. Most events of infusion-related reaction resolved either during or immediately after the infusion or by the next day. Two subjects (1 subject in the 750 mg MEDI3902 dose group and 1 subject in the 3000 mg dose group) did not complete dosing due to infusion-related reactions. No serious adverse events (SAEs) were reported.

PK and immunogenicity of MEDI3902 were studied in healthy adult volunteers in the Phase 1 study. Blood samples were collected predose and at various time points up to 60 days postdose for quantitating MEDI3902 concentrations in serum and for detecting ADA against MEDI3902. Following IV infusion, MEDI3902 exhibited linear PK in healthy adult subjects. Serum peak concentrations were observed immediately postinfusion, and declined in a bi-exponential manner over time. MEDI3902 concentrations in the 250 mg dose cohort were measurable up to 42 days postdose while other high-dose cohorts had measurable serum concentration through 60 days postdose. A single dose of 750 mg IV maintained serum exposure above the target level of 5.3 µg/mL for 28 days for most subjects in this cohort. MEDI3902 exposure in serum increased in an approximately dose-proportional manner from 250 mg to 1500 mg, and in a slightly less than dose proportional manner from 1500 mg to 3000 mg. $C_{max}$ increased from 100 µg/mL at 250 mg to 468 µg/mL at 1500 mg and to 838 µg/mL at 3000 mg. The area under the concentration-time curve from time zero to infinity ($AUC_\infty$) increased dose-proportionally from 694 µg·day/mL at 250 mg to 4246 µg·day/mL at 1500 mg. $ACU_\infty$ at 3000 mg was 6540 µg·day/mL. Serum terminal half-life was estimated to be 7-9 days. Volume of distribution at steady state ($Vd_{ss}$) was 3.4-4.9 L, indicating limited distribution into the extravascular space. Of the 42 subjects, 1 subject in Cohort 4 (3000 mg) tested ADA positive postdose on Day 61. The serum concentration of MEDI3902 in this subject rapidly decreased 45 days postdose and dropped to a level below the lower limit of quantification (LLOQ) 60 days postdose suggesting an impact of ADA on MEDI3902 PK.

MEDI3902 was found to be generally safe in the initial Phase 1 study.

Example 2

Clinical Trial Phase 2b Study

In the Phase 2, randomized, double-blind, placebo-controlled, single-dose, dose-ranging, proof-of-concept, approximately 429 subjects will be enrolled and dosed at approximately 120 sites primarily in Europe. Subjects will be randomly assigned in a 1:1:1 ratio to receive a single IV dose of 1500 mg or 3000 mg MEDI3902, or placebo. Dosing scheme can also be changed to a 1:1 randomization between single IV dose of MEDI3902 at 1500 mg (or 3000 mg) or placebo. Randomization will be stratified by geographic region and by whether subjects received anti-P. aeruginosa antibiotic treatment (duration of ≤72 hours) within the 96 hours prior to randomization. Subject will be followed through Day 50 (49 days post investigational produce administration) (FIG. 1).

In order to be enrolled, subjects are required to be 18 years of age or older, in the Intensive Care Unit, currently intubated and mechanically ventilated, and expected to remain intubated and mechanically ventilated for at least three days at the time of study entry. Subject must also be colonized with P. aeruginosa in the lower respiratory tract, as demonstrated by having a tracheal sample positive for P. aeruginosa within 36 hours prior to randomization, but are currently free of P. aeruginosa-related disease. Subjects with evidence of resolved pneumonia can be enrolled.

Subjects are not eligible to participate if they have acute confirmed or suspected Pseudomonas disease at enrollment or before receiving MEDI3902. Subjects are also not eligible to participate if they have previously received a monoclonal antibody, if they have a clinical pulmonary infection score (CPIS) of six or greater within the past 24 hours prior to MEDI3902 dosing, or if they have an Acute Physiology and Chronic Health Evaluation-II (APACHE-II) score of greater than or equal to 25 or a SOFA score of greater than or equal to 12 at time of randomization. Subjects with active pulmonary disease that would impair the ability to diagnose pneumonia (e.g., active tuberculosis or fungal disease, obstructing lung cancer, large pleural effusion or empyema, cystic fibrosis, or acute respiratory distress syndrome with lung "white out") are not eligible. Subjects who are tracheostomy-dependent prior to hospital admission and subjects with burns on more than 40% of body surface are not eligible. In addition, subjects are not eligible if they received an anti-P. aeruginosa antibiotic for more than 72 hours within 96 hours prior to randomization, wherein the antibiotic is considered active against the P. aeruginosa strain with which the subject is colonized, or wherein ongoing receipt of the anti-P. aeruginosa antibiotic is anticipated.

Subjects will be randomly assigned to receive a single dose of 1500 mg MEDI3902, 3000 mg MEDI3902, or placebo administered via IV infusion on Day 1. All subjects will be premedicated with antihistamine, for example, 50 mg diphenhydramine IV, clemastine 2 mg IV, or dexchlorpheniramine 5 mg IV (or another antihistamine preparation utilized in routine clinical practice for management of acute allergic reactions) within 15-30 minutes prior to start of study medication infusion. Additional premedication of subjects with acetaminophen 650 mg orally and/or methylprednisolone 20 mg IV in combination with the antihistamine, or the antihistamine together with famotidine 20 mg orally with or without acetaminophen and/or methylprednisolone prior to start of investigational produce infusion, can be authorized.

The primary efficacy endpoint for this study is the incidence of nosocomial pneumonia caused by P. aeruginosa through 21 days postdose (Day 22) after a single dose of MEDI3902 in mechanically ventilated subjects at risk for P. aeruginosa nosocomial pneumonia. The dosage levels were selected based on data from the Phase 1 study (see Example 1), PK/PD data from preclinical pharmacology studies (e.g., $EC_{90}$ in a murine P. aeruginosa-induced lethal pneumonia model), PK modelling based on observed increased clearance in ICU patients of other monoclonal antibodies directed at bacterial pathogens (FIG. 2), and a clinical report of median (range) time to VAP onset of 10 days. Some mechanically ventilated subjects will continue to require mechanical ventilation throughout the 21-day postdose period, but some subjects may be weaned off the ventilator during this period. Since these latter subjects may develop nosocomial pneumonia caused by P. aeruginosa after they no longer require mechanical ventilation, primary efficacy will be evaluated in subjects who were on mechanical ventilation at the time of enrolment, regardless of whether they remain on or are weaned off mechanical ventilation during the 21-day postdose period. The secondary efficacy endpoints will evaluate separately the incidence of nosocomial pneumonia caused by P. aeruginosa while on mechanical ventilation and the incidence of nosocomial pneumonia caused by P. aeruginosa after mechanical ventilation is no longer required through 21 days postdose.

The primary safety endpoints will assess TEAEs, TESAEs, and AESIs through 49 days postdose.

The secondary endpoints (MEDI3902 serum concentration, PK parameters, and ADA response to MEDI3902 through 49 days postdose) are designed to assess the presence of MEDI3902 in vivo.

Data analysis will be performed after all subjects have completed the study. Analysis of efficacy, pharmacokinetic (PK), anti-drug antibody (ADA), and safety will be performed on all data collected after the last subject has completed follow-up through 49 days postdose to demonstrate that a single IV dose of 1500 mg (and possibly 3000 mg) of MEDI3902 has an acceptable safety profile and is capable of reducing the incidence of P. aeruginosa pneumonia in mechanically ventilated subjects in the Intensive Care Unit (ICU) who are colonized with P. aeruginosa in the lower respiratory tract through 21 days postdose (irrespective of mechanical ventilation at the time of diagnosis).

Tracheal aspirate samples are collected for microbiological assessment of P. aeruginosa colonization on Days 2, 4(±1 day), 8(±1 day), 15(±1 day), 29(±1 day), and 50(±1 day), provided the subject remains intubated.

Subjects are monitored for clinical symptoms of pneumonia and other serious P. aeruginosa infection daily while in hospital, and in accordance with symptoms after hospital discharge. At these times, the monitoring includes a physical examination and evaluation of vital signs. While in the hospital, CPIS is assessed daily while the subject remains on mechanical ventilation.

For subjects with suspected serious P. aeruginosa infection, clinical symptoms (CPIS, SOFA, physical exam, and vital signs) are assessed at the day of onset and then daily through resolution. Blood samples are analyzed in all subjects with suspected serious P. aeruginosa infection on the day of onset and the two following days. Blood sampling analyses are repeated every other day in those that are positive for P. aeruginosa pneumonia until they are negative for P. aeruginosa. Tracheal or bronchial aspirates are analyzed in subjects with suspected serious P. aeruginosa infection that are intubated on the day of onset and the two following days. Tracheal or bronchial aspirates analyses are repeated every day in those that are positive for P. aeruginosa pneumonia until resolution. Expectorated sputum is analyzed in subjects with suspected serious P. aeruginosa infection that are not intubated (unless bronchoscopy performed for clinical management and BAL or PSB sample available) on the day of onset and the two following days. Expectorated sputum analyses are repeated every other day in those that are positive for P. aeruginosa pneumonia until resolution. Chest X-rays are performed on subjects with suspected serious P. aeruginosa infection on the day of onset. Chest X-rays are repeated in those with confirmed pneumonia as clinically indicated through resolution.

In subjects who are mechanically ventilated at the time of diagnosis of P. aeruginosa pneumonia, the criteria for the diagnosis requires that the subject demonstrate the following radiographic, clinical, and microbiologic new onset symptoms/signs that are not due to any other non-infectious cases.

1. Radiographic Criteria:
   a. New or worsening infiltrate consistent with pneumonia on chest x-ray obtained within 24 hours of the event (diagnosed by a qualified radiologist)
   AND
2. Clinical Criteria: At least 2 of the following minor or 1 major respiratory sign or symptom of new onset:
   Minor Criteria:
   b. Systemic signs of infection (one or more of the following): Abnormal temperature (oral or tympanic temperature >38° C. or a core temperature ≥38.3° C. or hypothermia, defined as a core body temperature of <35° C.), and/or abnormal WBC count (WBC count >10,000 cells/mm$^3$, WBC count <4,500 cells/mm$^3$, or >15% band neutrophils)
   c. Production of new purulent endotracheal secretions
   d. New physical examination findings consistent with pneumonia/pulmonary consolidation such as auscultatory findings (eg, rales, rhonchi, bronchial breath sounds) or dullness to percussion
   Major Criteria:
   e. Acute changes made in the ventilatory support system to enhance oxygenation, as determined by:
      i. PaO$_2$/FiO$_2$ ratio <240 mm Hg maintained for at least 4 hours OR
      ii. A decrease in PaO$_2$/FiO$_2$ by ≥50 mm Hg maintained for at least 4 hours
   AND
3. Microbiologic confirmation (obtained within 24 hours of onset of the event): At least 1 of the following:
   f. Respirator specimen positive for P. aeruginosa by culture includes a specimen of respiratory secretion obtained by endotracheal aspiration or by bronchoscopy with BAL or PSB sampling in intubated subjects. In subjects who are not intubated but meet the protocol definition of mechanical ventilation a specimen of expectorated sputum would be acceptable.
   g. Blood culture positive for P. aeruginosa (and no apparent primary source of infection outside the lung)
   h. Pleural fluid aspirate or lung tissue culture positive for P. aeruginosa during episode of pneumonia (only if obtained as part of the subject's accessary clinical management).

Subjects are considered mechanically ventilated if they are intubated with an endotracheal or nasotracheal tube and are receiving positive pressure ventilation support or if they are not intubated with an endotracheal or nasotracheal tube, but require 8 or more hours of positive pressure ventilation within the past 24 hours.

In subjects who are not mechanically ventilated at the time of diagnosis of P. aeruginosa pneumonia, the criteria for the diagnosis requires that the subject demonstrate the following radiographic, clinical, and microbiologic new onset symptoms/signs that are not due to any other noninfectious cases 4. Radiographic Criteria:
   i. New or worsening infiltrate consistent with pneumonia on chest x-ray obtained within 24 hours of the event (diagnosed by qualified radiologist)

AND
5. Clinical Criteria: At least 2 of the following minor or 1 major respiratory sign or symptom of new onset:

Minor criteria:
  j. Systemic signs of infection (one or more of the following): Abnormal temperature (oral or tympanic temperature >38° C. or a core temperature ≥38.3° C. or hypothermia, defined as a core body temperature of <35° C.) and/or abnormal WBC count (WBC count >10,000 cells/mm$^3$, WBC count <4,500 cells/mm$^3$, or >15% band neutrophils)
  k. A new onset of cough (or worsening of cough)
  l. Production of purulent sputum
  m. New physical examination findings consistent with pneumonia/pulmonary consolidation such as auscultatory findings (eg, rales, rhonchi, bronchial breath sounds) dullness to percussion, or pleuritic chest pain.
  n. Dyspnea tachypnea (respiratory rate >30 breaths/minute), or hypoxemia defined as:
    iii. Oxygen (O$_2$) saturation <90% or PaO$_2$<60 mm Hg on room air if lower than baseline, OR
    iv. A need to initiate or increase sustained (≥3 hours) supplemental O$_2$ to maintain pre-event baseline O$_2$ saturations Major Criteria:
  o. A need to initiate non-invasive mechanical ventilation or re-initiate invasive mechanical ventilation because of respiratory failure or worsening of respiratory status AND
6. Microbiologic confirmation (obtained within 72 hours of onset of the event): At least 1 of the following:
  p. Respiratory specimen positive for *P aeruginosa* by culture. Includes either expectorated sputum or (only if obtained as part of the subject's necessary clinical management) a specimen of respiratory secretions obtained by bronchoscopy with BAL or FSB sampling
  q. Blood culture positive for *P aeruginosa* (and no other apparent primary source of infection outside the lung)
  r. Pleural fluid aspirate or lung tissue culture positive for *P aeruginosa* (only if obtained as part of the subject's necessary clinical management).

A subject is not considered to be mechanically ventilated when an endotracheal or nasotracheal tube is not in place and the subject does not require positive ventilation support for at least 8 hours.

The incidence of *P. aeruginosa* pneumonia through 21 days post dose is calculated to demonstrate that administration of 1500 mg or 3000 mg MEDI3902 reduces the incidence of *P. aeruginosa* pneumonia. The incidence of *P. aeruginosa* pneumonia through 21 days post dose will be compared in subjects on mechanical ventilation and subjects in whom mechanical ventilation is no longer required.

Adverse events and new onset chronic disease are reviewed to demonstrate that an administration of 1500 or 3000 mg MEDI3902 is safe.

Example 3

MEDI3902 Reduces Lethality in Acute Pneumonia Model at Lower Bacterial Burden

The in vivo effect of MEDI3902 administration was studied in mice using an acute pneumonia model. Groups of mice (n=6) were injected intraperitoneally (IP) with either decreasing concentration of MEDI3902 (1.0 mg/kg, 0.5 mg/kg, or 0.2 mg/kg) or a isotype control IgG antibody (negative control, 0.75 mg/kg). Twenty-four hours after treatment, all mice were infected intranasally with 2×10$^5$ CFU *Pseudomonas aeruginosa* strain 6206 (1×LD$_{100}$). As shown in FIG. 3, all control treated animals succumbed to infection by 120 hours post infection. However, MEDI3902 showed complete protection across all doses, even at 1×LD$_{100}$, suggesting that a lower target serum level of 1.7 µg/mL in humans will provide protection across most strains of *P. aeruginosa*.

The breadth and scope of the present disclosure should not be limited by any of the above-described exemplary embodiments, but should be defined only in accordance with the following claims and their equivalents.

What is claimed is:

1. A method of treating a *Pseudomonas aeruginosa* infection in a susceptible human subject comprising administering to the subject 1500 mg or 3000 mg of a bispecific antibody that specifically binds *Pseudomonas aeruginosa* Psl and PcrV, wherein the bispecific antibody comprises a binding domain which specifically binds to *P. aeruginosa* Psl comprising a set of complementarity determining regions (CDRs): HCDR1-Psl, HCDR2-Psl, HCDR3-Psl, LCDR1-Psl, LCDR2-Psl, and LCDR3-Psl, wherein HCDR1-Psl has the amino acid sequence of SEQ ID NO: 10, HCDR2-Psl has the amino acid sequence of SEQ ID NO: 11, HCDR3-Psl has the amino acid sequence of SEQ ID NO: 12, LCDR1-Psl has the amino acid sequence of SEQ ID NO: 13, LCDR2-Psl has the amino acid sequence of SEQ ID NO: 14, and LCDR3-Psl has the amino acid sequence of SEQ ID NO: 15; and a binding domain which specifically binds to *P. aeruginosa* PcrV comprising a set of CDRs: HCDR1-PcrV, HCDR2-PcrV, HCDR3-PcrV, LCDR1-PcrV, LCDR2-PcrV, and LCDR3-PcrV, wherein HCDR1-PcrV has the amino acid sequence of SEQ ID NO: 2, HCDR2-PcrV has the amino acid sequence of SEQ ID NO: 3, HCDR3-PcrV has the amino acid sequence of SEQ ID NO: 4, LCDR1-PcrV has the amino acid sequence of SEQ ID NO: 6, LCDR2-PcrV has the amino acid sequence of SEQ ID NO: 7, and LCDR3-PcrV has the amino acid sequence of SEQ ID NO: 8, and wherein the subject maintains a serum concentration of the bispecific antibody of at least 1.7 µg/mL through 7 days following administration of the bispecific antibody.

2. The method of claim 1, wherein the infection is pneumonia, bacteremia, bone infection, joint infection, skin infection, burn infection, wound infection, or any combination thereof.

3. The method of claim 2, wherein the infection is pneumonia.

4. The method of claim 1, wherein the subject maintains a serum concentration of the bispecific antibody of at least 1.7 µg/mL through 21 days following administration of the bispecific antibody.

5. The method of claim 1, wherein the binding domain which specifically binds to P. aeruginosa Psl comprises an scFv comprising the amino acid sequence of SEQ ID NO:9.

6. The method of claim 1, wherein the binding domain which specifically binds to P. aeruginosa PcrV comprises a variable heavy chain comprising the amino acid sequence of SEQ ID NO:1 and a variable light chain comprising the amino acid sequence of SEQ ID NO:5.

7. The method of claim 1, wherein the bispecific antibody comprises (i) a heavy chain of the formula VH-CH1-H1-L1-S-L2-H2-CH2-CH3, wherein VH is an anti-P. aeruginosa PcrV heavy chain variable domain comprising the amino acid sequence of SEQ ID NO: 1; CH1 is a heavy chain constant region domain 1; H1 is a first heavy chain hinge region fragment; L1 is a first linker; S is an anti-P. aeruginosa Psl ScFv molecule comprising the amino acid sequence of SEQ ID NO: 9; L2 is a second linker; H2 is a second heavy chain hinge region fragment; CH2 is a heavy chain constant region domain-2; and CH3 is a heavy chain constant region domain-3; and (ii) a light chain of the formula VL-CL, wherein VL is an anti-P. aeruginosa PcrV light chain variable domain comprising the amino acid sequence of SEQ ID NO: 5, and CL is an antibody light chain kappa constant region or an antibody light chain lambda region.

8. The method of claim 1 wherein the infection is a nosocomial infection.

* * * * *

SEQUENCE LISTING

<160> NUMBER OF SEQ ID NOS: 24

<210> SEQ ID NO 1
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys

```
                85                  90                  95
Ala Lys Glu Glu Phe Leu Pro Gly Thr His Tyr Tyr Tyr Gly Met Asp
               100                 105                 110

Val Trp Gly Gln Gly Thr Thr Val Thr Val Ser Ser
           115                 120

<210> SEQ ID NO 2
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Tyr Ala Met Asn
1               5

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Ile Thr Met Ser Gly Ile Thr Ala Tyr Tyr Thr Asp Asp Val Lys
1               5                   10                  15

Gly

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Glu Phe Leu Pro Gly Thr His Tyr Tyr Tyr Gly Met Asp Val
1               5                   10                  15

<210> SEQ ID NO 5
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
```

```
                    85                  90                  95
Thr Phe Gly Gln Gly Thr Lys Val Glu Ile Lys
            100                 105

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Ala Ser Gln Gly Ile Arg Asn Asp Leu Gly
1               5                   10

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Ser Ala Ser Thr Leu Gln Ser
1               5

<210> SEQ ID NO 8
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Leu Gln Asp Tyr Asn Tyr Pro Trp Thr
1               5

<210> SEQ ID NO 9
<211> LENGTH: 246
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Pro Tyr
            20                  25                  30

Tyr Trp Thr Trp Ile Arg Gln Pro Pro Gly Lys Cys Leu Glu Leu Ile
        35                  40                  45

Gly Tyr Ile His Ser Ser Gly Tyr Thr Asp Tyr Asn Pro Ser Leu Lys
    50                  55                  60

Ser Arg Val Thr Ile Ser Gly Asp Thr Ser Lys Lys Gln Phe Ser Leu
65                  70                  75                  80

Lys Leu Ser Ser Val Thr Ala Ala Asp Thr Ala Val Tyr Tyr Cys Ala
                85                  90                  95

Arg Ala Asp Trp Asp Arg Leu Arg Ala Leu Asp Ile Trp Gly Gln Gly
            100                 105                 110
```

```
Thr Met Val Thr Val Ser Ser Gly Gly Gly Ser Gly Gly Gly
            115                 120                 125

Ser Gly Gly Gly Ser Gly Gly Gly Ser Asp Ile Gln Leu Thr
    130                 135                 140

Gln Ser Pro Ser Ser Leu Ser Ala Ser Val Gly Asp Arg Val Thr Ile
145                 150                 155                 160

Thr Cys Arg Ala Ser Gln Ser Ile Arg Ser His Leu Asn Trp Tyr Gln
                165                 170                 175

Gln Lys Pro Gly Lys Ala Pro Lys Leu Leu Ile Tyr Gly Ala Ser Asn
            180                 185                 190

Leu Gln Ser Gly Val Pro Ser Arg Phe Ser Gly Ser Gly Ser Gly Thr
            195                 200                 205

Asp Phe Thr Leu Thr Ile Ser Ser Leu Gln Pro Glu Asp Phe Ala Thr
    210                 215                 220

Tyr Tyr Cys Gln Gln Ser Thr Gly Ala Trp Asn Trp Phe Gly Cys Gly
225                 230                 235                 240

Thr Lys Val Glu Ile Lys
                245
```

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

```
Pro Tyr Tyr Trp Thr
1               5
```

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Tyr Ile His Ser Ser Gly Tyr Thr Asp Tyr Asn Pro Ser Leu Lys Ser
1               5                   10                  15
```

<210> SEQ ID NO 12
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Ala Asp Trp Asp Arg Leu Arg Ala Leu Asp Ile
1               5                   10
```

<210> SEQ ID NO 13
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Ala Ser Gln Ser Ile Arg Ser His Leu Asn
1               5                   10

<210> SEQ ID NO 14
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Gly Ala Ser Asn Leu Gln Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gln Gln Ser Thr Gly Ala Trp Asn Trp
1               5

<210> SEQ ID NO 16
<211> LENGTH: 98
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val

<210> SEQ ID NO 17
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Glu Pro Lys Ser Cys
1               5

<210> SEQ ID NO 18

```
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Lys Thr His Thr Cys Pro Pro Cys Pro
1               5                   10

<210> SEQ ID NO 19
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (22)..(22)
<223> OTHER INFORMATION: Met or Tyr
<220> FEATURE:
<221> NAME/KEY: MOD_RES
<222> LOCATION: (24)..(24)
<223> OTHER INFORMATION: Ser or Thr
<220> FEATURE:
<221> NAME/KEY: MOD_RES
<222> LOCATION: (26)..(26)
<223> OTHER INFORMATION: Thr or Glu

<400> SEQUENCE: 19

Ala Pro Glu Leu Leu Gly Gly Pro Ser Val Phe Leu Phe Pro Pro Lys
1               5                   10                  15

Pro Lys Asp Thr Leu Xaa Ile Xaa Arg Xaa Pro Glu Val Thr Cys Val
                20                  25                  30

Val Val Asp Val Ser His Glu Asp Pro Glu Val Lys Phe Asn Trp Tyr
            35                  40                  45

Val Asp Gly Val Glu Val His Asn Ala Lys Thr Lys Pro Arg Glu Glu
        50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
130                 135                 140

Ser Asp Ile Ala Val Glu Trp Glu Ser Asn Gly Gln Pro Glu Asn Asn
145                 150                 155                 160

Tyr Lys Thr Thr Pro Pro Ser Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 20
```

-continued

```
<211> LENGTH: 217
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215

<210> SEQ ID NO 21
<211> LENGTH: 720
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Asn Trp Val Arg Gln Ala Pro Gly Lys Gly Leu Glu Trp Val
        35                  40                  45

Ser Ala Ile Thr Met Ser Gly Ile Thr Ala Tyr Tyr Thr Asp Asp Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Lys Glu Glu Phe Leu Pro Gly Thr His Tyr Tyr Gly Met Asp
        100                 105                 110

Val Trp Gly Gln Gly Thr Thr Val Thr Val Ser Ser Ala Ser Thr Lys
        115                 120                 125

Gly Pro Ser Val Phe Pro Leu Ala Pro Ser Ser Lys Ser Thr Ser Gly
130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Arg Val Glu Pro
    210                 215                 220

Lys Ser Cys Gly Gly Gly Gly Ser Gly Gly Gly Ser Gln Val Gln
225                 230                 235                 240

Leu Gln Glu Ser Gly Pro Gly Leu Val Lys Pro Ser Glu Thr Leu Ser
                245                 250                 255

Leu Thr Cys Thr Val Ser Gly Gly Ser Ile Ser Pro Tyr Tyr Trp Thr
            260                 265                 270

Trp Ile Arg Gln Pro Pro Gly Lys Cys Leu Glu Leu Ile Gly Tyr Ile
        275                 280                 285

His Ser Ser Gly Tyr Thr Asp Tyr Asn Pro Ser Leu Lys Ser Arg Val
    290                 295                 300

Thr Ile Ser Gly Asp Thr Ser Lys Lys Gln Phe Ser Leu Lys Leu Ser
305                 310                 315                 320

Ser Val Thr Ala Ala Asp Thr Ala Val Tyr Tyr Cys Ala Arg Ala Asp
                325                 330                 335

Trp Asp Arg Leu Arg Ala Leu Asp Ile Trp Gly Gln Gly Thr Met Val
            340                 345                 350

Thr Val Ser Ser Gly Gly Gly Gly Ser Gly Gly Gly Ser Gly Gly
        355                 360                 365

Gly Gly Ser Gly Gly Gly Ser Asp Ile Gln Leu Thr Gln Ser Pro
    370                 375                 380

Ser Ser Leu Ser Ala Ser Val Gly Asp Arg Val Thr Ile Thr Cys Arg
385                 390                 395                 400

Ala Ser Gln Ser Ile Arg Ser His Leu Asn Trp Tyr Gln Gln Lys Pro
                405                 410                 415

Gly Lys Ala Pro Lys Leu Leu Ile Tyr Gly Ala Ser Asn Leu Gln Ser
            420                 425                 430

Gly Val Pro Ser Arg Phe Ser Gly Ser Gly Ser Gly Thr Asp Phe Thr
        435                 440                 445

Leu Thr Ile Ser Ser Leu Gln Pro Glu Asp Phe Ala Thr Tyr Tyr Cys
    450                 455                 460

Gln Gln Ser Thr Gly Ala Trp Asn Trp Phe Gly Cys Gly Thr Lys Val
465                 470                 475                 480

Glu Ile Lys Gly Gly Gly Gly Ser Gly Gly Gly Gly Ser Asp Lys Thr
                485                 490                 495

His Thr Cys Pro Pro Cys Pro Ala Pro Glu Leu Leu Gly Gly Pro Ser
            500                 505                 510
```

-continued

Val Phe Leu Phe Pro Pro Lys Pro Lys Asp Thr Leu Met Ile Ser Arg
            515                 520                 525

Thr Pro Glu Val Thr Cys Val Val Val Asp Val Ser His Glu Asp Pro
    530                 535                 540

Glu Val Lys Phe Asn Trp Tyr Val Asp Gly Val Glu Val His Asn Ala
545                 550                 555                 560

Lys Thr Lys Pro Arg Glu Glu Gln Tyr Asn Ser Thr Tyr Arg Val Val
                565                 570                 575

Ser Val Leu Thr Val Leu His Gln Asp Trp Leu Asn Gly Lys Glu Tyr
            580                 585                 590

Lys Cys Lys Val Ser Asn Lys Ala Leu Pro Ala Pro Ile Glu Lys Thr
        595                 600                 605

Ile Ser Lys Ala Lys Gly Gln Pro Arg Glu Pro Gln Val Tyr Thr Leu
    610                 615                 620

Pro Pro Ser Arg Glu Glu Met Thr Lys Asn Gln Val Ser Leu Thr Cys
625                 630                 635                 640

Leu Val Lys Gly Phe Tyr Pro Ser Asp Ile Ala Val Glu Trp Glu Ser
                645                 650                 655

Asn Gly Gln Pro Glu Asn Asn Tyr Lys Thr Thr Pro Pro Val Leu Asp
            660                 665                 670

Ser Asp Gly Ser Phe Phe Leu Tyr Ser Lys Leu Thr Val Asp Lys Ser
        675                 680                 685

Arg Trp Gln Gln Gly Asn Val Phe Ser Cys Ser Val Met His Glu Ala
    690                 695                 700

Leu His Asn His Tyr Thr Gln Lys Ser Leu Ser Leu Ser Pro Gly Lys
705                 710                 715                 720

<210> SEQ ID NO 22
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Leu Leu Ile
        35                  40                  45

Tyr Ser Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 23
<211> LENGTH: 25
<212> TYPE: PRT
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: MISC_FEATURE
<222> LOCATION: (1)..(25)
<223> OTHER INFORMATION: This sequence may encompass 0-5 'Gly Gly Gly
      Gly Ser' repeating units

<400> SEQUENCE: 23

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      linker sequence
<220> FEATURE:
<221> NAME/KEY: MISC_FEATURE
<222> LOCATION: (1)..(20)
<223> OTHER INFORMATION: This sequence may encompass 0-5 'Gly Gly Gly
      Gly' repeating units

<400> SEQUENCE: 24

Gly Gly Gly Gly Gly Gly Gly Gly Gly Gly Gly Gly Gly Gly Gly Gly
1               5                   10                  15

Gly Gly Gly Gly
            20
```